United States Patent
Kessous et al.

(10) Patent No.: US 6,617,103 B1
(45) Date of Patent: Sep. 9, 2003

(54) IDENTIFICATION OF A TRANSFORMING FRAGMENT OF HERPES SIMPLEX TYPE 2 AND DETECTION THEREOF IN CLINICAL SPECIMENS

(75) Inventors: Allegria Kessous, Côte St-Luc (CA); François Coutlée, Montréal (CA); Joseph A. Dipaolo, Bethesda, MD (US)

(73) Assignees: The United States of America as represented by the Department of Health and Human Services, Washington, DC (US); Universite de Montreal

( * ) Notice: Subject to any disclaimer, the term of this patent is extended or adjusted under 35 U.S.C. 154(b) by 0 days.

(21) Appl. No.: 09/202,918

(22) PCT Filed: Jun. 30, 1997

(86) PCT No.: PCT/CA97/00470
§ 371 (c)(1),
(2), (4) Date: Aug. 13, 1999

(87) PCT Pub. No.: WO98/00567
PCT Pub. Date: Jan. 8, 1998

Related U.S. Application Data

(60) Provisional application No. 60/020,957, filed on Jul. 1, 1996.

(51) Int. Cl.$^7$ .............................. C12Q 1/70; C12Q 1/68; C07K 14/035
(52) U.S. Cl. ................................ 435/5; 435/6; 530/350
(58) Field of Search ..................... 435/5, 6; 536/23.72, 536/24.32, 24.33; 530/350

(56) References Cited

FOREIGN PATENT DOCUMENTS

WO    WO 95/06055    3/1995

OTHER PUBLICATIONS

Carter et al., 1996, Journal of Virology 70:7663–7668.
Chomczynski et al., 1987, Anal. Biochem. 162:156–159.
Corbino et al., 1989, Eur. J. Gynaec. Oncol. 10:103–108.
Daling et al., 1996, Cancer Epid., Biom. & Prev. 5:541–548.
Danik et al., 1991, Cancer Det. and Prev. 15:107–113.
Gleaves et al., 1985, Journal of Clin. Microb. 21:29–32.
Guibinga et al., 1995, Arch. STD/HIV Res. 9:163–179.
Guibinga et al., 1996, J. Clin. Microbiol. 34:1654–1659.
Kane et al., 1989, Gene 84:439–446.
Kessler et al., 1986, In: Viral Etiology of Cervical Cancer. Peto, R., zur Hauzen, H. eds. Cold Spring Harbor, New York, 55–64.
Kessous–Elbaz, 1989, J. Gen. Virol. 70:2171–2177.
Kimura et al., 1990, Med. Microbiol. Immunol. 179:177–184.
Kriesel et al., 1994, J. Clin. Microbiol. 32:3088–3090.
Lafferty et al., 1987, New Engl. J. Med. 316:1444–1449.
Lakeman et al., 1995, J. Infectious Diseases171:857–863.
Macnab et al., 1987, J. Gen. Virol. 68:2525–2550.
Macnab et al., 1989, Biomed. and Pharmac. 43:167–172.
McGeoch et al., 1988, J. Gen. Virol. 69:1531–1574.
Park et al., 1983, EMBO J. 2:1029–1034.
Rawls et al., 1968, Am. J. Epidemiol. 87:647–655.
Saavedra et al., 1985, EMBO J. 4:3419–3426.
Sanger et al., 1977, Proc. Natl. Acad. Sci. 74:5463–5467.
Swain et al., 1985, J. Virol. 53:561–569.
Ward et al., 1996, Journal of Virol. 70(5):2684–2690.

*Primary Examiner*—Donna C. Wortman
(74) *Attorney, Agent, or Firm*—Knobbe, Martens, Olson & Bear LLP

(57) ABSTRACT

The present invention relates to oligonucleotide probes derived from HSV-2, capable of selectively hybridizing thereto and to a subsequence of HSV-2 BglII N from which the oligonucleotide probes were derived. Further, the invention relates to an optimized assay of nudeic acid amplification permitting the sensitive and specific detection in clinical specimens of HSV-2 as well as a specific typing of the HSV in the sample. The present invention further relates to kits for the detection and typing of the HSV in a sample. In addition, the invention provides the nucleic acid and amino acid sequence of a subsequence of HSV-2 BglII N having transforming activity. Further, the invention teaches diagnostic and therapeutic methods for genital cancer comprising the use of these sequences or ligands directed thereto.

8 Claims, 9 Drawing Sheets

```
     Xho2 sequence and oRF
   1 CTCGAGGGCC AGGCCCGGGT CCCGCCCGCG TTCCCGGAAC CGCCGGGAAC CAAGCGGAGG   60
  61 CACGCCGGGG CCGAAGTTGT TCCCCGCGGA CGACGCCACC AAGGCCCGAA GACGGCTGCC  120
 121 CGCCGGCCCC CACGCGAGCC GAGTCGCCCC CCCTCTCCGC GAGATACGGA CCCGAGGCGG  180
 181 CGGAGGGTGG TGGGGACGGC GGCGCTATCG CGTGCTACTT TCGCGACCTC CAGACCGGCG  240
 241 ACGCGAGCCC CAGCCCCCTC TCCGCCTTCC GGGGTCCCCC AAAGACCCCA TACGGCTTTG  300
 301 GGTTGCCTGA CGGACGACGG GTGGTGGCCG AACGCTTCAC GCGCCCGGGC ACGCGGGGTG  360
 361 CGTTGTGTTA AAAAAATAAA TAAATGGGGT AGTGTGTCCC CCCCCTCCAA CCAATATGGC  420
 421 TGTCGTGTGT GGTTCCGGGT TGCGCCTCCG TCCTTTCCAC CCCCCTTCCC CCTCCTTTTT  480
 481 TGTTTTGCGT GCGCTTATAA GACGCCCCG GGGCCCTTCG CAGCTTCACC GAGAGCGCCG  540
 541 TCGGGCCCCG GGTGCGGGAT GTGTCGCGGG GACAGCCCCG GGGTCGCGGG CGGGACGGGC  600
                                                        M   C   R   G   D   S   P   G   V   A   G   T   G
 601 <u>GAACACTGCC TCGGAGGGGA TGAT</u>GGGGAC GACGGGCGCC CCCGCCTCGC CTGCGTGGGT  660
      E   H   C   L   G   G   D   D   G   D   D   G   R   P   R   L   A   C   V   G
 661 GCCATCGCTC GGGGGTTCGC GCATCTCTGG CTCCAGGCCA CCACGCTGGG <u>CTTCGTGGGG</u>  720
      A   I   A   R   G   F   A   H   L   W   L   Q   A   T   T   L   G   F   V   G
 721 <u>TCTGTCGTTC</u> TGTCGCGCGG CCCGTATGCG GACGCCATGT CGGGGGCGTT <u>CGTGATCGGG</u>  780
      S   V   V   L   S   R   G   P   Y   A   D   A   M   S   G   A   F   V   I   G
 781 <u>AGCACCGGCC</u> TGGGGTTCCT CCGCGCCCCC CCCGCGTTCG CCCGGCCGCC GACGCGTGTG  840
      S   T   G   L   G   F   L   R   A   P   P   A   F   A   R   P   P   T   R   V
 841 TGCGCGTGGC TGAGGCTGGT CGGCGGGGGA GCGGCCGTGG CCCTGTGGAG CCTCGGGGAG  900
      C   A   W   L   R   L   V   G   G   G   A   V   A   L   W   S   L   G   E
 901 GCCGGCGCGC CTCCGGGGGT TCCGGGCCCG GCGACCCAGT GCCTGGCGCT CGGGGCCGCC  960
      A   G   A   P   P   G   V   P   G   P   A   T   Q   C   L   A   L   G   A   A
 961 TACGCGGTGC TGGTGCTGGC CGACGACGTC CATCCCCTTT TCCTCCTCGC CCCGCGGCCC 1020
      Y   A   L   L   V   L   A   D   D   V   H   P   L   F   L   L   A   P   R   P
1021 CTGTTTGTCG GCACCCTGGG GGTTGTCGTC GGCGGGCTGA CGATAGGCGG CAGTGCGCGC 1080
      L   F   V   G   T   L   G   V   V   V   G   G   L   T   I   G   G   S   A   R
1081 TACTGGTGGA TCGACCCCCG CGCCGCCGCG GCCCTGACGG CGGCGGTGGT GGCGGGCCTC 1140
      Y   W   W   I   D   P   R   A   A   A   L   T   A   V   V   A   G   L
1141 GGGACAACCG CCGCCGGGGA CAGCTTTTCC AAGGCCTGTC CCCGCCACCG CCGCTTTTGC 1200
      G   T   T   A   A   G   D   S   F   S   K   A   C   P   R   H   R   R   F   C
1201 GTCGTCTCCG CGGTCGAGTC TCCCCCGCCC CGATACGCCC CGGAGGACGC CGAGCGGCCA 1260
      V   V   S   A   V   E   S   P   P   P   R   Y   A   P   E   D   A   E   R   P
1261 ACAGACCACG GACCCCTGTT ACCGTCGACG CACCACCAGC GATCTCCGCG GGTCTGCGGC 1320
      T   D   H   G   P   L   L   P   S   T   H   H   Q   R   S   P   R   V   C   G
1321 GACGGGGCCC GACGCGAAAA CATCTGGGTT CCCGTGGTGA CCTTTGCGGG CGCGCTCGCG 1380
      D   G   A   R   R   E   N   I   W   V   P   V   V   T   F   A   G   A   L   A
1381 CTGGCCGCCT GCGCCGCGCG AGGGTCTGAC GCGGCTCCGT CAGGCCCGGT CCTGCCGCTG 1440
      L   A   A   C   A   A   R   G   S   D   A   A   P   S   G   P   V   L   P   L
1441 TGGCCCCAGG TGTTTGTCGG GGCCACGCG GCGGCGGGCC TGACGGAGCT GTGTCAGACC 1500
      W   P   Q   V   F   V   G   G   H   A   A   A   G   L   T   E   L   C   Q   T
1501 CTCGGCCCCC GGGACCTCAC GGACCCGCTG CTGTTTGCGT ACGTCGGATT CCAGGTCGTG 1560
      L   G   P   R   D   L   T   D   P   L   L   F   A   Y   V   G   F   Q   V   V
1561 AACCACGGGC TGATGTTTGT GGTCCCCGAC ATCGCCGTAT ACGCGATGCT GGGGGGCGCC 1620
      N   H   G   L   M   F   V   V   P   D   I   A   V   Y   A   M   L   G   G   A
1621 GTGTGGATCT CGCTGACGCA GGTGCTTGGG CTCCGGCGCC GCCTTCACAA GGACCCAGAC 1680
      V   W   I   S   L   T   Q   V   L   G   L   R   R   R   L   H   K   D   P   D
1681 GCCGGGCCCT GGGCGGCCGC GACCCTGCGG GGCCTCTTTT TCTCCGTCTA CGCATTGGGG 1740
      A   G   P   W   A   A   A   T   L   R   G   L   F   F   S   V   Y   A   L   G
1741 TTTGCGGCGG GGTGCTGGT GCGGCCGCGG ATGGCGGCGA GCCGGCGGTC GGGGTGATCG 1800
      F   A   A   G   V   L   V   R   P   R   M   A   A   S   R   R   S   G   *
1801 CCATTTCAAA TAAAAGGCAC GAGTTCCCCG AATACCACCG GCGTGTGATG ATTTCGCCCT 1860
1861 ACCGCTCCGA TCCCCGGGGG GAGGGGGGAA GGAAATGGGG GCGGGGGTGC CGTGGACGGG 1920
1921 TATAAAGGCC AGGGGGGCAG GCGGGCCCAT CACTGTTAGG GTGTTAGGTT GGGAGGTGGC 1980
1981 ACAAAAAGCG ACACACCCGT GTTGTAGTTG TCCGCGGGAG GCGGTGGTTT CCGGCAACCC 2040
2041 TCCTCGCTGC GCCGGGCGCG CCCACCGGTC CTTCGCGGGG GCCGGGGCTC TTCTGGTCAT 2100
2101 GGCCCTTGGA CGGGTGGGCC TAGCCGTGGG CCTGTGGGGC CTGCTGTGGG TGGGTGTGGT 2160
2161 CGTGGTGCTG GCCAATGCCT CCCCCGGACG CACGATAACG GTGGGCCCGC GGGGGAACGC 2220
2221 GAGCAATGCC GCCCCCTCCG CGTCCCCGCG AACGCATCC GCCCCCCGAA CCACACCCAC 2280
2281 GCCCCCCCAA CCCCGCAAGG CGACGAAAAG TAAGGCCTCC ACCGCCAAAC CGGCCCCGCC 2340
2341 CCCCAAGACC GGGCCCCCGA AGACATCCTC GGAGCCCGTG CGATGCAACC GCCACGACCC 2400
2401 GCTGGCCCGG TACGGCTCGC GGGTGCAAAT CCGATGCCGG TTTCCCAACT CCACCCGCAC 2460
2461 GGAGTCCCGC CTCCAGATCT                                              2480
```

FIG. 8

SEQUENCE LISTING

```
<160> NUMBER OF SEQ ID NOS:  5

<210> SEQ ID NO 1
<211> LENGTH: 2480
<212> TYPE: DNA
<213> ORGANISM: Unknown Organism
<220> FEATURE:
<221> NAME/KEY: CDS
<222> LOCATION: (559)..(1794)
<223> OTHER INFORMATION: Description of Unknown Organism: HSV-2

<400> SEQUENCE: 1
ctcgagggcc aggcccgggt cccgcccgcg ttcccggaac cgccgggaac caagcggagg       60
cacgccgggg ccgaagttgt tccccgcgga cgacgccacc aaggcccgaa gacggctgcc      120
cgccggcccc cacgcgagcc gagtcgcccc ccctctccgc gagatacgga cccgaggcgg      180
cggagggtgg tggggacggc ggcgctatcg cgtgctactt tcgcgacctc cagaccggcg      240
acgcgagccc cagcccctc tccgccttcc ggggtccccc aaagacccca tacggctttg       300
ggttgcctga cggacgacgg gtggtggccg aacgcttcac gcgcccgggc acgcggggtg      360
cgttgtgtta aaaaaataaa taaatggggt agtgtgtccc cccctccaa ccaatatggc       420 tgtcgtgtgt ggttccgggt tgcgcctccg tcctttccac cccccttccc cctccttttt      480
tgttttgcgt gcgcttataa gacgcgcccg gggcccttcg cagcttcacc gagagcgccg      540
tcgggccccg ggtgcggg atg tgt cgc ggg gac agc ccc ggg gtc gcg ggc        591
                     Met Cys Arg Gly Asp Ser Pro Gly Val Ala Gly
                      1               5                  10 ggg acg ggc gaa cac tgc ctc gga ggg gat gat ggg gac gac ggg cgc        639
Gly Thr Gly Glu His Cys Leu Gly Gly Asp Asp Gly Asp Asp Gly Arg
             15                  20                  25 ccc cgc ctc gcc tgc gtg ggt gcc atc gct cgg ggg ttc gcg cat ctc        687
Pro Arg Leu Ala Cys Val Gly Ala Ile Ala Arg Gly Phe Ala His Leu
         30                  35                  40 tgg ctc cag gcc acc acg ctg ggc ttc gtg ggg tct gtc gtt ctg tcg        735
Trp Leu Gln Ala Thr Thr Leu Gly Phe Val Gly Ser Val Val Leu Ser
     45                  50                  55 cgc ggc ccg tat gcg gac gcc atg tcg ggg gcg ttc gtg atc ggg agc        783
Arg Gly Pro Tyr Ala Asp Ala Met Ser Gly Ala Phe Val Ile Gly Ser
 60                  65                  70                  75 acc ggc ctg ggg ttc ctc cgc gcc ccc ccc gcg ttc gcc cgg ccg ccg        831
Thr Gly Leu Gly Phe Leu Arg Ala Pro Pro Ala Phe Ala Arg Pro Pro
                 80                  85                  90
```

```
acg cgt gtg tgc gcg tgg ctg agg ctg gtc ggc ggg gga gcg gcc gtg      879
Thr Arg Val Cys Ala Trp Leu Arg Leu Val Gly Gly Gly Ala Ala Val
         95                 100                 105 gcc ctg tgg agc ctc ggg gag gcc ggc gcg cct ccg ggg gtt ccg ggc      927
Ala Leu Trp Ser Leu Gly Glu Ala Gly Ala Pro Pro Gly Val Pro Gly
        110                 115                 120 ccg gcg acc cag tgc ctg gcg ctc ggg gcc gcc tac gcg gtg ctg gtg      975
Pro Ala Thr Gln Cys Leu Ala Leu Gly Ala Ala Tyr Ala Val Leu Val
        125                 130                 135 ctg gcc gac gac gtc cat ccc ctt ttc ctc ctc gcc ccg cgg ccc ctg     1023
Leu Ala Asp Asp Val His Pro Leu Phe Leu Leu Ala Pro Arg Pro Leu
140                 145                 150                 155 ttt gtc ggc acc ctg ggg gtt gtc gtc ggc ggg ctg acg ata ggc ggc     1071
Phe Val Gly Thr Leu Gly Val Val Val Gly Gly Leu Thr Ile Gly Gly
            160                 165                 170 agt gcg cgc tac tgg tgg atc gac ccc cgc gcc gcc gcg gcc ctg acg     1119
Ser Ala Arg Tyr Trp Trp Ile Asp Pro Arg Ala Ala Ala Ala Leu Thr
            175                 180                 185 gcg gcg gtg gtg gcg ggc ctc ggg aca acc gcc gcc ggg gac agc ttt     1167
Ala Ala Val Val Ala Gly Leu Gly Thr Thr Ala Ala Gly Asp Ser Phe
        190                 195                 200 tcc aag gcc tgt ccc cgc cac cgc cgc ttt tgc gtc gtc tcc gcg gtc     1215
Ser Lys Ala Cys Pro Arg His Arg Arg Phe Cys Val Val Ser Ala Val
        205                 210                 215 gag tct ccc ccg ccc cga tac gcc ccg gag gac gcc gag cgg cca aca     1263
Glu Ser Pro Pro Pro Arg Tyr Ala Pro Glu Asp Ala Glu Arg Pro Thr
220                 225                 230                 235 gac cac gga ccc ctg tta ccg tcg acg cac cac cag cga tct ccg cgg     1311
Asp His Gly Pro Leu Leu Pro Ser Thr His His Gln Arg Ser Pro Arg
            240                 245                 250 gtc tgc ggc gac ggg gcc cga cgc gaa aac atc tgg gtt ccc gtg gtg     1359
Val Cys Gly Asp Gly Ala Arg Arg Glu Asn Ile Trp Val Pro Val Val
            255                 260                 265 acc ttt gcg ggc gcg ctc gcg ctg gcc gcc tgc gcc gcg cga ggg tct     1407
Thr Phe Ala Gly Ala Leu Ala Leu Ala Ala Cys Ala Ala Arg Gly Ser
        270                 275                 280 gac gcg gct ccg tca ggc ccg gtc ctg ccg ctg tgg ccc cag gtg ttt     1455
Asp Ala Ala Pro Ser Gly Pro Val Leu Pro Leu Trp Pro Gln Val Phe
285                 290                 295 gtc ggg ggc cac gcg gcg gcg ggc ctg acg gag ctg tgt cag acc ctc     1503
Val Gly Gly His Ala Ala Ala Gly Leu Thr Glu Leu Cys Gln Thr Leu
300                 305                 310                 315 ggc ccc cgg gac ctc acg gac ccg ctg ctg ttt gcg tac gtc gga ttc     1551
Gly Pro Arg Asp Leu Thr Asp Pro Leu Leu Phe Ala Tyr Val Gly Phe
            320                 325                 330 cag gtc gtg aac cac ggg ctg atg ttt gtg gtc ccc gac atc gcc gta     1599
Gln Val Val Asn His Gly Leu Met Phe Val Val Pro Asp Ile Ala Val
            335                 340                 345 tac gcg atg ctg ggg ggc gcc gtg tgg atc tcg ctg acg cag gtg ctt     1647
Tyr Ala Met Leu Gly Gly Ala Val Trp Ile Ser Leu Thr Gln Val Leu
        350                 355                 360 ggg ctc cgg cgc cgc ctt cac aag gac cca gac gcc ggg ccc tgg gcg     1695
Gly Leu Arg Arg Arg Leu His Lys Asp Pro Asp Ala Gly Pro Trp Ala
        365                 370                 375 gcc gcg acc ctg cgg ggc ctc ttt ttc tcc gtc tac gca ttg ggg ttt     1743
Ala Ala Thr Leu Arg Gly Leu Phe Phe Ser Val Tyr Ala Leu Gly Phe
380                 385                 390                 395 gcg gcg ggg gtg ctg gtg cgg ccg cgg atg gcg gcg agc cgg cgg tcg     1791
Ala Ala Gly Val Leu Val Arg Pro Arg Met Ala Ala Ser Arg Arg Ser
            400                 405                 410
```

-continued

```
ggg tgatcgccat ttcaaataaa aggcacgagt tccccgaata ccaccggcgt    1844
Gly gtgatgattt cgccctaccg ctccgatccc cggggggagg ggggaaggaa atggggggcgg   1904 gggtgccgtg gacgggtata aaggccaggg gggcaggcgg gcccatcact gttagggtgt   1964
taggttggga ggtggcacaa aaagcgacac acccgtgttg tagttgtccg cgggaggcgg   2024
tggtttccgg caaccctcct cgctgcgccg ggcgcgccca ccggtccttc gcggggggccg   2084 gggctcttct ggtcatggcc cttggacggg tgggcctagc cgtgggcctg tggggcctgc   2144
tgtgggtggg tgtggtcgtg gtgctggcca atgcctcccc cggacgcacg ataacggtgg   2204
gcccgcgggg gaacgcgagc aatgccgccc cctccgcgtc cccgcggaac gcatccgccc   2264
cccgaaccac acccacgccc ccccaacccc gcaaggcgac gaaaagtaag gcctccaccg   2324
ccaaaccggc cccgcccccc aagaccgggc ccccgaagac atcctcggag cccgtgcgat   2384
gcaaccgcca cgaccgctg gcccggtacg gctcgcgggt gcaaatccga tgccggtttc   2444
ccaactccac ccgcacggag tcccgcctcc agatct                             2480
```

<210> SEQ ID NO 2
<211> LENGTH: 412
<212> TYPE: PRT
<213> ORGANISM: Unknown Organism
<220> FEATURE:
<223> OTHER INFORMATION: Description of Unknown Organism: HSV-2

<400> SEQUENCE: 2

```
Met Cys Arg Gly Asp Ser Pro Gly Val Ala Gly Gly Thr Gly Glu His
  1               5                  10                  15

Cys Leu Gly Gly Asp Asp Gly Asp Gly Arg Pro Arg Leu Ala Cys
                 20                  25                  30

Val Gly Ala Ile Ala Arg Gly Phe Ala His Leu Trp Leu Gln Ala Thr
             35                  40                  45

Thr Leu Gly Phe Val Gly Ser Val Leu Ser Arg Gly Pro Tyr Ala
         50                  55                  60

Asp Ala Met Ser Gly Ala Phe Val Ile Gly Ser Thr Gly Leu Gly Phe
 65                  70                  75                  80

Leu Arg Ala Pro Pro Ala Phe Ala Arg Pro Pro Thr Arg Val Cys Ala
                 85                  90                  95

Trp Leu Arg Leu Val Gly Gly Gly Ala Ala Val Ala Leu Trp Ser Leu
            100                 105                 110

Gly Glu Ala Gly Ala Pro Pro Gly Val Pro Gly Pro Ala Thr Gln Cys
        115                 120                 125

Leu Ala Leu Gly Ala Ala Tyr Ala Val Leu Val Leu Ala Asp Asp Val
130                 135                 140

His Pro Leu Phe Leu Leu Ala Pro Arg Pro Leu Phe Val Gly Thr Leu
145                 150                 155                 160

Gly Val Val Gly Gly Leu Thr Ile Gly Gly Ser Ala Arg Tyr Trp
                165                 170                 175

Trp Ile Asp Pro Arg Ala Ala Ala Leu Thr Ala Ala Val Val Ala
            180                 185                 190

Gly Leu Gly Thr Thr Ala Ala Gly Asp Ser Phe Ser Lys Ala Cys Pro
        195                 200                 205

Arg His Arg Arg Phe Cys Val Val Ser Ala Val Glu Ser Pro Pro
    210                 215                 220

Arg Tyr Ala Pro Glu Asp Ala Glu Arg Pro Thr Asp His Gly Pro Leu
```

```
                    225                 230                 235                 240
Leu Pro Ser Thr His His Gln Arg Ser Pro Arg Val Cys Gly Asp Gly
                245                 250                 255

Ala Arg Arg Glu Asn Ile Trp Val Pro Val Thr Phe Ala Gly Ala
            260                 265                 270

Leu Ala Leu Ala Ala Cys Ala Ala Arg Gly Ser Asp Ala Ala Pro Ser
            275                 280                 285

Gly Pro Val Leu Pro Leu Trp Pro Gln Val Phe Val Gly Gly His Ala
        290                 295                 300

Ala Ala Gly Leu Thr Glu Leu Cys Gln Thr Leu Gly Pro Arg Asp Leu
305                 310                 315                 320

Thr Asp Pro Leu Leu Phe Ala Tyr Val Gly Phe Gln Val Val Asn His
                325                 330                 335

Gly Leu Met Phe Val Val Pro Asp Ile Ala Val Tyr Ala Met Leu Gly
                340                 345                 350

Gly Ala Val Trp Ile Ser Leu Thr Gln Val Leu Gly Leu Arg Arg Arg
                355                 360                 365

Leu His Lys Asp Pro Asp Ala Gly Pro Trp Ala Ala Thr Leu Arg
    370                 375                 380

Gly Leu Phe Phe Ser Val Tyr Ala Leu Gly Phe Ala Ala Gly Val Leu
385                 390                 395                 400

Val Arg Pro Arg Met Ala Ala Ser Arg Arg Ser Gly
                405                 410

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
aacactgcct cggagcggat gat                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
aggccggtgc tcccgatcac gaa                                              23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ttcgtggggt ctgtcgttct g                                                21
```

IDENTIFICATION OF A TRANSFORMING FRAGMENT OF HERPES SIMPLEX TYPE 2 AND DETECTION THEREOF IN CLINICAL SPECIMENS

This application is a 371 of International Application No. PCT/CA97/00470 filed Jun. 30, 1997, which claims the benefit of priority of U.S. patent application Ser. No. 60/020,957 filed Jul. 1, 1996.

FIELD OF THE INVENTION

The present invention relates to the detection of Herpes Simplex type 2 (HSV-2), more particularly, the invention relates to a transforming fragment of HSV-2 and to the detection thereof in clinical specimens.

BACKGROUND OF THE INVENTION

Nearly one fifth of adults in the United States are infected with herpes simplex virus type 2 (HSV-2). Although HSV-2 is the most common cause of genital ulceration in developed countries, subclinical HSV-2 infections are suspected to affect a more important proportion of infected individuals. HSV-2 has also been proposed as a causative agent of genital cancer (Guibinga et al., 1995, Arch. STD/HIV Res. 9:163–179). However conflicting results from in vitro and in vivo studies have shed doubts on the role of this agent in cancer of the uterine cervix (Guibinga et al., 1995, Arch. STD/HIV Res. 9:163–179). A transforming region of the HSV-2 genome—the 7.6 kb BglII N (m.u. 0.58–0.63) segment—has been identified, using transfection experiments. This was further supported by studies showing that BglII N sequences can also cooperate with oncogenic papillomas viruses to transform cells (DiPaolo et al., 1990, Virol. 777–779). Initially, the transforming ability of HSV-2 was thought to be located on the left-end (Xho-3 subfragment) of the BglII N segment (Galloway et al., 1983, Nature 392:21–24; Ibid., 1984, Proc. Natl. Acad. Sci. USA 81:4736–4740). However, neither the presence of a viral protein (Galloway et al., 1982, J. Virol. 42:530–537; Vonka et al., 1987, Adv. Cancer Res. 48:149–191) nor the persistence or integration (Galloway et al., 1983; Vonka et al., 1987) of specific HSV sequences, seemed to be required for the maintenance of the transformed phenotype (Pilon et al., 1989, Biochem. Biophys. Res. Comm. 159:1249–1261). The transforming ability of HSV-2 was left unexplained. Transfection of NIH 3T3 cells with the right-end (Kessous-Elbaz et al., 1989, J. Gen. Virol. 70:2171–2177; Pilon et al., 1989; Saavedra et al., 1985, EMBO J. 4:3419–3426) of the BglII N fragment (the Xho-1 and Xho-2 subfragments) showed an increase in the number of transformed foci, and HSV-2 sequences were retained more efficiently in transformed cells (Kessous-Elbaz et al., 1989; Pilon et al., 1989; Saavedra et al., 1985).

A number of clinical and epidemiologic studies have concluded that high risk papillomaviruses, such as HPV-16 and HPV-18 are necessary for the development of cervical cancer, but the long delay following infection indicates the importance of other factors (Kessler, 1986, In: Viral Etiology of Cervical Cancer, Peto et al., Eds. Cold Spring Harbor, N.Y., 55–64; and, zur Hauzen, 1989, Cancer Research 49:46774681), particularly other sexually transmitted infections (Kaufman et al., 1986, Clin. Obstet. Gynecol. 29:678–698; Macnab et al., 1989, Biomed. and Pharmacother. 43:167–172; zur Hausen, 1982, Lancet 2:1370–1372), for the development of malignancy. Although the etiologic link between herpes simplex virus-2 (HSV-2) and cervical cancer was proposed over two decades ago, the significance of the importance of HSV-2 to cervical cancer has been rather recent. The role for HSV-2 infection has been based primarily on sero-epidemiological data (Nahmias et al., 1970, Am. J. Epidemiol. 91:547–552; Rawls et al., 1968, Am. J. Epidemiol. 87:647–656) and on observation of viral antigens in exfoliated cells from patients with cervical dysplasia and cancer (Royston et al., 1970, Proc. Nat. Acad. Sci. 67:204–212). The difficulty in establishing a strong association was compounded by the lack of persistence of HSV sequences in the neoplastic cervical lesions (Macnab et al., 1989, Biomed. and Pharmacother. 43:167–172). In fact, in a prospective case-control study (Vonka, 1984, Int. J. Cancer 33:61–65) the investigators failed to observe such an association, which was later suggested may have resulted from overmatching of the cohort of women for sexual activity that minimized the risk factor (Reeves et al., 1989, New Engl. J. Med. 320:1437–1441). In other studies the lack of correlation of HSV-2 with cervical cancer was attributed to the use of immunoglobulin G instead of immunoglobulin A as a marker for the presence of HSV-2 (Corbino et al., 1989, Eur. J. Gynaecol. Oncol. 10:103–108).

A recent case-control study, using confirmed histological cases of cervical cancer from Latin America, found that the presence of HSV-2 antibodies correlated with a nine-fold excess risk of cervical cancer compared to women negative for HSV-2 or HPV-16/18 (Hildesheim et al., 1991, Int. J. Cancer 49:335–340). In well controlled studies of cervical cancer, others have reported a two-to-four fold excess risk in HSV-2 seropositive women (Slattery et al., 1989, Amer. J. Epidemiol. 130:248–258) and in women with both HPV and HSV-2 present in cervical tumor biopsies (Di Luca et al., 1989, Int. J. Cancer 43:570–577; Ibid., 1987, Int. J. Cancer 40:763–768.). Finally, in the last case control study (Daling et al., 1996, Cancer Epidemiology, Biomarkers and Prevention 5:541–548), involving women from western Washington state, the potential cofactors with HPVs in the development of cervical cancer were analysed. A significant increase in risk associated with HSV-2, as measured by antibodies, was found only in women whose tumor biopsies were negative for HPV. One major problem in establishing a definite link between HSV-2 and cervical cancer has been the difficulty to consistently detect HSV-2-specific DNA in cervical cancer biopsy samples despite the fact that several investigators have reported the presence of herpes virus specific sequences in some of the carcinomas tissues they have analysed (Frenkel et al., 1972, Proc. Nat. Acad. Sci. 69:3784–3789; Park et al., 1983, EMBO J. 2:1029–1034; Royston et al., 1970, Proc. Nat. Acad. Sci. 67204–212).

Experimental support for a role of HSV-2 in cervical cancer has come from in vitro studies that demonstrated its transforming potential using the inactivated virus (Duff et al., 1971, Nature 233:48–50; Macnab, 1974, J. Gen. Virol. 24:143–153) or its fragments, BglII N (mtr II) and BglII C (mtrIII) (Galloway et al., 1981, J. Virol. 38:749–760; Jariwalla et al., 1980, Proc. Natl. Acad. Sci. (USA) 77:2279–83; Reyes et al., 1979, Cold Spring Harbor Symp. Quant. Biol. 44:629–641). However the elucidation of the mechanism(s) leading to the transformed phenotype has been complicated by the loss of the viral sequences, which suggested the hypothesis of hit and run mechanism (Galloway et al., 1983, Nature 302:21–24) and review (Macnab et al., 1987, J. Gen. Virol. 68:2525–2550). Our studies on the transforming potential and the retention of BglII N and its XhoI restricted subfragments have suggested that BglII N, when present in its entirety, might have a toxic effect resulting from either a high copy number or from specific function(s) expressed by its coding sequences (Saavedra et al., 1985, EMBO J. 4:3419–3426). These studies also demonstrated that two BglII N subfragments—Xho-1+2 and Xho-2—induced the tumorigenic conversion of NIH3T3 cells and were stably retained in the transformed cell lines and their derived tumors (Saavedra et al., 1985, EMBO J. 4:3419–3426). The role of HSV-2 in cervical cancer has been further supported by in vitro studies showing its oncogenic cooperation with HPV 16/18. HPV-16 immortalized human foreskin keratinocytes transfected with a recombinant plasmid bearing the HSV-2 fragment BglII N yielded tumorigenic clones, whereas the parental HPV-immortalized cell lines were incapable of inducing tumors. Southern blot analysis of the viral sequences present in the transformed cell lines indicated that HPV-16 genomes were maintained unchanged in their integrated state, but HSV-2 sequences were not found in the tumor-derived cell lines (DiPaolo et al., 1990, Virology 177:777–779). Using a similar approach, Dhanwada et al. (Dhanwada et al., 1993, J. Gen. Virol. 74:955–963; Ibid., 1992, J. Gen. Virol. 73791–799) showed that HSV-2 mtrIII (BglII C) region induced rearrangements of HPV-18 DNA sequences in the immortalized human keratinocytes and chromosomal changes in HPV-16-immortalized human cell lines but did not produce the tumorigenic conversion observed with mtrII. Three of five HPV-18/HSV-2 cell lines retained the HSV-2 mtrIII DNA.

The sum of these recent clinical, epidemiological and experimental data is suggestive that HSV-2 might contribute to cervical cancer in women who are also infected with HPV-16/18. However, the exact role of herpes infection in the development of the cervical tumors still remains unclear.

There still remains a need to identify a molecular determinant of HSV-2 that cooperates with HPV to promote the development of cervical tumors. There also remains a need to identify the subfragment of HIV-2 BglII which could be responsible for the promotion of the tumorigenic conversion in human cervical cells. Finally, there remains a need to identify the role of HSV-2 BglII.

The diagnosis of HSV-2 infection is commonly performed using cell culture on appropriate clinical specimens (Gleaveset al., 1985, J. Clin. Microbiol. 21:29–32). However, the ability to isolate HSV-2 in cell culture is reduced in old lesions, in the presence of an host immune response and in episodes of reactivation (Lafferty et al., 1987, New Engl. J. Med. 316:1444–1449). In recent years, the use of the polymerase chain reaction (PCR) has allowed for the detection of HSV-2 DNA in diseases for which cell culture failed to establish a diagnosis, such as herpes simplex encephalitis (Kimura et al., 1991, J. Inf. Dis. 164:289–293; Lakeman et al., 1995, J. Inf. Dis. 171:857–863). Since it does not require the presence of infectious viral particles, PCR has also demonstrated the presence of viral DNA in culture-negative specimens (Cone et al., 1991, J. Inf. Dis. 164:757–760; Kimura et al., 1990, Med. Microbiol. Immunol. 179:77–84; Kriesel et al., 1994, J. Clin. Microbiol. 32:3088–3090; Nahass et al., 1992, JAMA 268:2541–2544; Rogers et al., 1992, Obstet. Gynecol. 79:464–469). PCR (or other amplification methods) could thus prove useful for the analysis of specimens sent to the laboratory from remote clinics. PCR (or other amplification methods) could also identify asymptomatic shedding of HSV-2 (Hardy et al., 1990, J. Inf. Dis. 162:1031–1035), a clinical situation where the titer of HSV is reduced (Corey et al., 1988, Microbiol. Infect. Dis. 4 (Suppl.): 111S–119S). PCR assays amplifying sequences from the left-end of BglII N have been described (Lulitanond et al., 1994, Mol. Cell Probes 8:441–447; Yamakawa et al., 1994, APMIS 102:401–406). These studies demonstrated that in opposite to normal tissue, precancerous of cancerous lesions of the uterine cervix contained specific HSV-2 DNA sequences. However, the use of the left-end of BglII N does not provide the sensitivity required for proper detection of HSV-2 infection in uterine cervix cancer. Indeed, the left-end of BglII N is often lost in these cancer cells, thereby leading to false negative results.

There thus remains a need for the development and optimization of an assay, for the specific detection in clinical specimens of HIV-2 specific sequences. There also remains a need for a tool for the specific detection of transforming sequences of HSV-2 from the right end of BglII N and more generally for the typing of the HSV infection in question.

SUMMARY OF THE INVENTION

The invention provides, in general, isolated nucleic acid molecules coding for Xho-2 or fragments thereof.

The invention further provides purified Xho-2 polypeptides or an epitope binding portion thereof.

The invention also provides nucleic acids for the specific detection of the presence of nucleic acids encoding Xho-2 proteins or polypeptides in a sample.

The invention further provides a method of detecting nucleic acid encoding Xho-2 in a sample.

The invention also provides a kit for detecting the presence of nucleic acid encoding Xho-2 in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides an antisense Xho-2 nucleic acid molecule.

The invention also provides a cell that contains the above-described recombinant nucleic acid molecule.

The invention further provides a non-human organism that contains the above-described recombinant nucleic acid molecule.

The invention also provides an antibody having binding affinity specifically to Xho-2 or an epitope-bearing portion thereof.

The invention further provides a method of detecting Xho-2 in a sample.

The invention also provides a method of measuring the amount of Xho-2 in a sample.

The invention further provides a method of detecting antibodies having binding affinity specifically to Xho-2.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for human disease, in particular, genital cancer. Preferably, a method of diagnosing the presence or predisposition to develop genital cancer in a patient is provided herein.

The invention also provides methods for therapeutic uses involving all or part of (1) a nucleic acid sequence encoding Xho-2, (2) antisense Xho-2 nucleic acid molecules, (3) Xho-2 protein, or (4) Xho-2 antibodies.

Further objects and advantages of the present invention will be clear from the description that follows.

More particularly, this invention concerns the cloning and nudeic acid sequencing of the Xho-2 subfragment of BglII N, located at the right end of BglII N of HSV-2 and to probes derived therefrom. From this sequence, primers that specifically detect sequences from this region were identified. These nucleic acid sequences can be used in diagnostic procedures, to identify the type of HSV present in a given biological sample. Further, these nucleic acid sequences provide the additional advantage of permitting the identification of the HSV-2 molecular determinant responsible for the transformation activity of HSV-2 in vivo, the right end of BglII N. The invention also concerns methods using these nucleic acid sequences as well as kits comprising same.

The invention also relates to an optimized and validated assay for the investigation of the role of HSV-2 as a cofactor in genital cancer, more specifically, cervical cancer. It also relates to the development and optimization of an amplification assay for the specific detection in clinical specimens of transforming sequences of HSV-2 from the right end of BglII N. In a preferred embodiment, it relates to a PCR assay therefor. Various clinical isolates of herpes viruses were evaluated in vitro in this PCR assay. The optimized PCR assay was then compared with cell culture for the detection of HSV-2 infection in specimens collected from various sites and submitted to the diagnostic laboratory for viral culture.

The invention also relates to the Xho-2 fragment having a sequence of 2480 bp and encoding an open reading frame (ORF) specifying a putative protein of 413aa. The invention thus also refers to the Xho-2 protein, antibodies thereto and to ligands which specifically bind thereto. In a related aspect, the invention also relates to the use of the Xho-2 nucleic acid or protein sequence or parts or derivatives thereof to transform an immortalized cell. Therefore, the present invention relates to a model for the analysis of the contribution of HSV-2 complete or potential sequences to cervical cancer and more particularly, to its complementation with HPV.

In addition, the present invention relates to the Xho-2 nucleic acid sequence, Xho-2 protein fragments or derivatives thereof as targets for a diagnosis of HSV-2 presence and potentially of prognosis of cervical cancer.

The applicant has determined the sequence of the Xho-2 fragment of BlgII N. Having identified regions of HSV-2 Xho-2 which are specific thereto, the applicant is the first to provide a means of obtaining diagnostic tools for the typing of HSV viruses. By demonstrating that Xho-2 has a transforming capacity or oncogenic function in HPV-immortalized cervical cells, the applicant is thus the first to have identified the HSV-2 molecular determinant responsible for the transformation activity of HSV-2 in genital cancer. In so doing, the applicant is the first to have derived a cellular model of cervical cancer. The applicant has also derived three probes from the Xho-2 nucleic acid sequence which enable a sensitive (down to 10 copies and even less in a preferred embodiment) and specific (without cross-reactivity with other HSV, human genomic sequence or HPV) assay for the detection and identification of HSV-2 sequences in a sample such as a biological sample.

It will be-clear to a person of ordinary skill, to which this application pertains, that in the context of a diagnostic test, the nucleic acid sequences of the present invention, although preferably used in the context of an amplification method which permits an increase in sensitivity of detection and identification, can also be used in hybridization experiments such as, for example, Southern blots or Northern blots.

It should be noted that because of the G-C content, the obtention of probes or primers, which display the sensitivity and specificity (HSV-2-specific) of those described herein, is complexified. However, by providing the nucleic acid sequence of Xho-2, the applicant enables the design of additional primer pairs or probes which could demonstrate the same level of sensitivity and specificity as probes disclosed hereinbelow. Additional probes or primers displaying adequate specificity and sensitivity can be obtained in accordance with the present invention or in accordance with other well known methods. These probes and primers could be tested in accordance to the present invention and according to known methods to verify their specificity and sensitivity.

It will also be understood that the use of PCR technology to amplify the targeted HSV-2 sequence is only a preferred method of amplification, as other methods are well known to a person of ordinary skill (see below). Accordingly, the present invention cannot be limited to a particular type of amplification method.

Nucleotide sequences are presented herein by single strand only, in the 5' to 3' direction, from left to right. One letter nucleotide symbols used herein have their standard meaning in the art in accordance with the recommendations of the IUPAC-IUB Biochemical Nomenclature Commission.

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule: An "isolated nucleic acid molecule", as is generally understood and used herein, refers to a polymer of nucleotides, and includes but should not be limited to DNA and RNA. The "isolated" nucleic acid molecule is purified from its natural in vivo state.

Recombinant DNA: Any DNA molecule formed by joining DNA segments from different sources and produced using recombinant DNA technology (a.k.a. molecular genetic engineering).

DNA Segment: A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

The term "amplification pair": As used herein, refers to a pair of oligonucleotides of the present invention selected to be suitable for use together in amplifying a selected HSV-2 nucleic acid sequence by an amplification process such as polymerase chain reaction, ligase chain reaction, strand displacement amplification, or nucleic acid sequence-based amplification, as explained in greater detail below.

Nucleic acid (i.e., DNA or RNA) samples for practicing the present invention may be obtained from any suitable source. Typically, the nucleic acid sample will be obtained in the form of a clinical sample of a biological fluid or biological tissue to be assessed as containing the HSV-2 sequences. It will be apparent that the present invention also permits the detection of HSV-2 nucleic acid sequences in non-clinical samples. Suitable clinical samples include, but are not limited to, genital and non-genital samples.

Oligonucleotide probes or primers of the present invention may be of any suitable length, depending on the particular assay format employed. In general, the oligonucleotide probes or primers are at least 15 nucleotides in length. For example, oligonucleotide probes or primers used for detecting HSV-2 are preferably about 20 nucleotides in length. The oligonucleotide probes or primers may be adapted to be especially suited to a chosen nucleic acid amplification system.

Nucleic Acid Hybrdization: Nudeic add hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. The DNA of the individual to be tested can be digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., Current protocols in Molecular Biology, John Wily & Sons, Inc., New York, N.Y. (1989). A nitrocellulose filter is incubated overnight at 68° C. with labeled probe in a solution containing 50% formamide, high salt (either 5×SSC[20×: 3M NaCl/0.3M trisodium citrate] or 5×SSPE [20×: 3.6M NaCl/0.2M NaH$_2$PO$_4$/0.02M EDTA, pH 7.7]), 5×Denhardt's solution, 1% SDS, and 100 µg/ml denatured salmon sperm DNA This is followed by several washes in 0.2×SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Stringent conditions (e.g., conditions represented by a wash stringency of 0.5×SSC and 0.1% SDS at a temperature of 20 or 30 degrees below the melting temperature of the probe or even conditions represented by a wash stringency of 0.1×SSC and 0.1% SDS at a temperature of 10 degrees below the melting temperature of the duplex of probe and target nucleic acid in a standard hybridization assay) will be preferably used; see J. Sambrook et al., Molecular Cloning, A Laboratory manual, 2d Ed. 1989, Cold Spring Harbor Laboratory.

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally illustrated by Miller ,1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), with DNA preferred.

Use of probes in detection methods include Northern blots (RNA detection), Southern blots (DNA detection), western blots (protein detection), and dot or slot blots (DNA, RNA or protein). Other detection methods include kits containing probes on a dipstick setup and the like.

Hybrid molecules formed from using the probes of the invention can be detected by using a detectable marker which is added to one of the probes. Probes can be labeled by several methods. Probes can be radiolabeled and detected by autoradiography. Such labels for autoradiography include $^3$H, $^{125}$I, $^{35}$S, $^{14}$C, and $^{32}$P. Typically, the choice of radioactive isotopes depends on research preferences involving ease of synthesis, stability, and half lives of the isotopes. Non-limiting examples of detectable markers include ligands, fluorophores, chemiluminescent agents, electrochemical via sensors, time-resolved fluorescence, enzymes, and antibodies. For example, an antibody can be labeled with a ligand. Other detectable markers for use with probes of the invention include biotin, radionucdeotides, enzyme inhibitors, co-enzymes, luciferins, paramagnetic metals, spin labels, and monoclonal antibodies. The choice of label dictates the manner in which the label is bound to the probe.

Radioactive nucleotides can be incorporated into probes of the invention by several means. Such means include nick translation of double-stranded probes, copying single-stranded M13 plasmids having specific inserts with the Klenow fragment of DNA polymerase I of E. coli or other such DNA polymerase in the presence of radioactive dNTP, transcribing CDNA from RNA templates using reverse transcriptase in the presence of radioactive dNTP, transcribing RNA from vectors containing strong promoters such as SP6 promoters or T7 promoters using SP6 or T7 RNA polymerase in the presence of radioactive rNTP, tailing the 3' ends of probes with radioactive nucleotides using terminal transferase, and by phosphorylation of the 5' ends of probes using gamma $^{32}$P ATP and polynucleotide kinase.

Oligonucleotide or Oligomer: A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Amplification Primer: An oligonucleotide which is capable of annealing adjacent to a target sequence and serving as an initiation point for DNA synthesis when placed under conditions in which synthesis of a primer extension product which is complementary to a nucleic acid strand is initiated.

Amplification of a selected, or target, nucleic acid sequence may be carried out by any suitable means. See generally Kwoh et al., 1990, Am. Biotechnol. Lab. 8:14–25. Examples of suitable amplification techniques include, but are not limited to, polymerase chain reaction, ligase chain reaction, strand displacement amplification, transcription-based amplification (see Kwoh et al., 1989, Proc. Natl. Acad. Sci. USA 86, 1173–1177), self-sustained sequence replication (see Guatelli et al., 1990, Proc. Natl. Acad. Sci. USA 87, 1874–1878), the Qβ replicase system (see Lizardi et al., 1988, BioTechnology 6:1197–1202) and NASBA (Malek et al., 1994, Methods Mol. Biol., 28:253–260). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions. An extension product of each primer which is synthesized is complementary to each nucleic acid strand, with the primers sufficiently complementary to each strand of the specific sequence to hybridize therewith. The extension product which is synthesized from each primer, when separated from its complement, can then serve as a template for the synthesis of the extension product of the other primer. The sample is then treated under denaturing conditions to separate the primer extension products from their templates and the sample analyzed to assess whether the sequence or sequences to be detected are present. These steps are cyclically preferred until the desired degree of amplification is obtained. Detection of the amplified sequence may be carried out by adding to the reaction product an oligonucleotide probe capable of hybridizing to the reaction product (e.g. an oligonucleotide probe of the present invention), the probe carrying a detectable label, and then detecting the label in accordance with known techniques.

Ligase chain reaction (LCR) is carried out in accordance with known techniques (Weiss, 1991, Science 254:1292. Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392–396; and Ibid., 1992, Nucleic Acids Res. 20:1691–1696.

Vector: A plasmid or phage DNA or other DNA sequence into which DNA of the present invention can be inserted to be cloned. The vector can replicate autonomously in a host cell, and can be further characterized by one or a small number of endonuclease recognition sites as well as preferably a marker suitable for use in the identification of cells transformed with the vector. The words "cloning vehicle" are sometimes used for "vector."

Expression: Expression is the process by which a structural gene produces a polypeptide. It involves transcription of the gene into mRNA, and the translation of such mRNA into polypeptide(s).

Expression Vector: A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative: A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutcal Sciences* (1980). Procedures for coupling such moieties to a molecule are well known in the art.

Variant: A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele: An "allele" is an alternative form of a gene occupying a given locus on the chromosome.

Mutation: A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

Purified: A "purified" protein or nucleic acid is a protein or nucleic acid that has been separated from a cellular component. "Purified" proteins or nucleic acids have been purified to a level of purity not found in nature.

Substantially Pure: A "substantially pure" protein or nucleic acid is a protein or nucleic acid preparation that is lacking in all other cellular components.

A kit for detecting HSV-2 nucleic acid in a clinical sample contains at least one nucleic acid sequence of the present invention, and hybridization solution for enabling hybridization between this sequence and the nucleic acid sample, with the nucleic acid sequence either suspended in the solution or provided separately in lyophilized form. One example of a suitable hybridization solution is a solution comprised of 6×SSC (0.9M sodium chloride, 0.09M sodium citrate, pH7.0), 0.1M EDTA pH 8.0, 5×Denhardt's solution [0.1% (w/v) Ficoll™ Type 400, 0.1% (w/v) polyvinylpyrrolidone, 0.1% (w/v) bovine serum albumin], and 100 $\mu$g/ml sheared, denatured salmon sperm DNA, commercially available from Bethesda Research Laboratories, Gaithersburg, Md. 20877 USA under Catalog No. 5565UA. See also Sambrook et al., 1989, A Laboratory Manual, 2nd Edition, 387–388, Cold Spring Harbor Laboratory. For example, the components of the kit are packaged together in a common container (e.g., a container sealed with a frangible seal), the kit typically including an instruction sheet for carrying out a specific embodiment of the method of the present invention. Additional optional components of the kit, depending on the assay format to be employed, include a second nucleic acid sequence of the invention suitable for use with the first sequence for carrying out PCR as explained above (or, in the case of a kit for carrying out LCR, two pairs of probes or primers of the present invention), none, one or more detection probes, and means for carrying out a detecting step (e.g., a probe or primer of the invention labelled with a detectable marker and optionally an enzyme substrate when the detectable marker is an enzyme).

It should be understood that having now recognized that the Xho-2 nucleic acid segment is transforming in the contact of an HPV-immortalized cervical cell, and hence it can complement HPV and transform same, inhibitors of the Xho-2 transforming activity could be screened and identified using the genital cancer cell line of the invention.

By "antisense molecules" is meant nudeic acid fragments which are complementary to their target and eventually lead an inhibition of the production of the protein encoded by this target. These antisense can be small segments of nucleic acids or long ones. They can also comprise modifications which enhance their stability. The design of appropriate antisense molecules and derivatives thereof is well known to an artisan of ordinary skill. These antisense against Xho-2 can be tested for their effects on the transforming activity of Xho-2 in accordance with the present invention or other suitable methods. In one embodiment, the full antisense Xho-2 nucleic acid sequence could be used. In a preferred embodiment, complementary regions to the coding sequence of Xho-2 could be used as antisense.

Other objects, advantages and features of the present invention will become more apparent upon reading of the following non restrictive description of preferred embodiments thereof, given by way of example only with reference to the accompanying drawings.

BRIEF DESCRIPTION OF THE DRAWINGS

In the appended drawings:

FIG. 8 shows the nudeofide anrd amino acid sequence of Xho-2.

DETAILED DESCRIPTION OF THE INVENTION

1—MATERIALS AND METHODS

Cell Cultures and Plasmids

Figure 1:
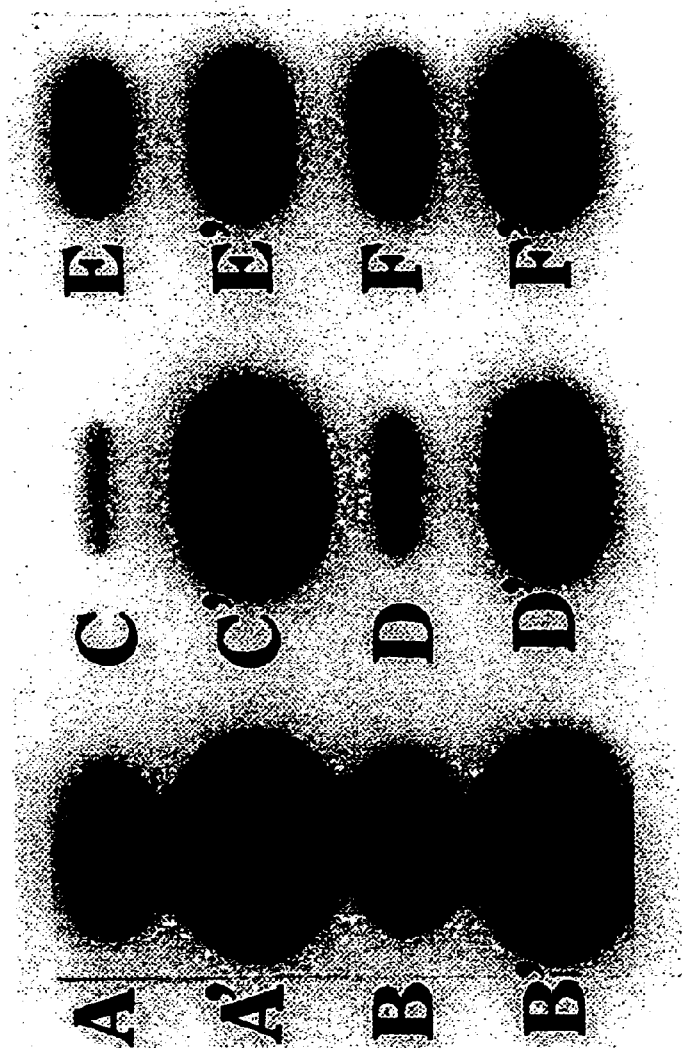
FIG. 1 shows the influence of the denaturation time on the efficiency of PCR to amplify Xho-2. Various HSV-2 templates were amplified with Xho-2 PCR using a one minute denaturation step (A-F) or a two minute denaturation step (A'-F'). Amplified products were detected with radiolabeled Xho-p. The HSV-2 templates amplified were: 10,000 copies (A,A') and 3,300 copies (B,B') of pXho-1+2, and four clinical specimens contained in viral transport medium (C,C'; D,D'; E,E'; F,F')

Previously a series of immortalized cell lines were obtained by transfection with recombinant HPV-16 or -18 DNA and by selection with the neomycin resistance gene (Pirisi et al., 1987, J. Virol. 61:1061–1066). Cell line HPVGS originally had been derived from foreskin epithelial cells and the other epithelial cell lines (CX16-2, CX16-5, CX18-1) were independently derived from the squamous transformation zone of the cervix. All cell lines had HPV-16 or -18 integrated into the cellular DNA. Cell lines were grown in MCDB-153-LB with the exception of HPVGS which was grown in F-12/Dulbecco (1:1) with 5 percent fetal bovine serum. All cultures were in 100 mm plastic dishes in a humidified 5 percent $CO_2$ incubator. These cell lines although immortalized and positive for integrated HPV-16 or -18 fail to produce tumors in nude mice, even after 150 passages at 1 to 10 splits. An additional control consisted of normal secondary culture of foreskin-derived epithelial cells transfected with the plasmids. The plasmids used in the transfection experiments were derived by insertion of the XhoI restricted fragments Xho1+2 and Xho-2 of BglII N into the pHC79 plasmid, as previously described (Saavedra et al., 1985, EMBO J. 4:3419–3426). The plasmid pHaMDR (Kane et al., 1989, Gene 84:439–446) carrying the multidrug resistance gene mdr1 that prevents the accumulation of toxic drugs including colchicine, was used for selection of the transfectants.

Transfection

The HPV immortalized epithelial cell lines derived from either foreskin (HPVGS) or cervix (CX16-2, CX16-5 and CX18-1) were used at high passage (20–40) for transfection with either pXho-2, pXho1+2 or the control vector pHC79. Because the HPV immortalized cells had been selected for neomycin resistance, an alternate selection method was required for transfection with the pXho DNAs. Therefore, the plasmid harboring the mdr 1 gene was cotransfected with the pXho DNAs or the control vector pHC79. This results in the prevention of accumulation of toxic drugs including colchicine. The cell lines (40–60 percent confluent) were cotransfected with 10 mg of each Xho DNA plasmids or control pHC79 and 2 mg of pHaMDR using lipofectin reagent (Life Technologies, Gaithersburg, Md.). Briefly, 12 mg of DNA was added to 1 ml of basal MCDB-153-LB medium (lacking peptide growth factors, hydrocortisone and bovine pituitary extract), mixed briefly, and 40 ml of lipofectin reagent were added. The mixture was incubated 20 minutes with mixing every five minutes and then added to a cell monolayer in a 100 mm dish. Cultures were rocked every 20 minutes for 2 hours, 5 ml of complete medium was added and cultures were incubated overnight. The cultures were then subpassaged into 3×100 mm dishes and 24 hours later were treated with MCDB-153-LB containing colchicine (10–30 ng/ml) until colonies were visible (approximately 2 weeks). Individual clones (C) were picked using cloning pipettes or colonies from a dish were trypsinized and pooled (M) to establish cells lines.

Tumorigenicity Testing

For tumorigenicity assays, cells were removed from the dish with trypsin-versene, washed in serum-containing medium, centrifuged and resuspended in serum-free medium. Four representative cell lines previously transfected with pXho-2, pXho1+2 and control pHC79 were used. Cells ($5 \times 10^6$ to $10^7$) in <0.1 ml were injected subcutaneously into 3 to 7 day-old Beige Nude or SCID mice. A minimum of five mice were used for each series of injections. Animals were monitored daily for palpable tumors. When a tumor mass was observed, the animal was killed by cervical dislocation and the tumor removed. As control, the HPV-immortalized parental cell lines were maintained in culture and tested for tumor formation using the same conditions.

DNAs Analyses

The presence of the HSV-2 Xho-2 and Xho1+2 in the transfected cells and their respective controls was investigated using Southern blot hybridization. DNA was extracted from cell pellets by overnight lysis in 0.5% SDS and 100 mg/ml proteinase K at 37° C. DNAs were purified with phenol/chloroform and chloroform and then precipitated with ethanol. Twenty micrograms of cellular DNA were digested with BamHI, electrophoresed in 0.7% agarose gel, transferred to nylon membranes and probed with the Xho-2 fragment radioactively labeled using [$a^{32}P$] dCTP (ICN) and the random-primer method (Boehringer Mannheim Co.). The hybridization reaction was carried out at 42° C. for 12 hours in 50% (vol/vol) formamide, 6×SSPE, 10×Denhardt solution, 1% SDS, 10% dextran sulfate and 50 mg/ml of denatured salmon sperm DNA. The filters were washed under highly stringent conditions at 65° C. in 0.1×SSPE, 0.1% SDS. Autoradiographic exposures were made at −80° C.

Primer sequences were selected from the sequence data of Xho-2 subfragment of BglII N (SEQ. ID. No.:1—see below).

Polymerase chain reaction (PCR) was used to detect Xho-2 DNA in tumors. The DNA was purified from paraffin-embedded tumor sections as follows: 15 mm sections were deparaffinized in 1 ml xylene and the tissue pellet was harvested by centrifugation at 12,000 g for 2 min. After rinses in ethanol 100% and acetone, the tissue samples were dried and digested with 200 mg/ml proteinase K in 50 mM Tris-HCl, ph 8.5, 1 mM EDTA, 1% Tween-20™ at 55° C. for 2–3 hrs. The proteinase K was then heat-inactivated at 95° C. for 10 mn. The samples were clarified from debris and then amplified with Xho-a and Xho-b primers as previously described (Guibinga et al., 1996, J. Clin. Microbiol. 34:1654–1659). The amplified products were hybridized with $\alpha^{32}P$-labeled Xho-p internal probe. As controls, the same reactions were carried out on samples with no DNA or with 2 ng pXho-2. The sequence of the primers and probe was as follows:

Xho-a (upstream primer):
5'-AACACTGCCTCGGAGGGGATGAT-3',
SEQ. ID. No.:3;

Xho-b (downstream primer):
5'-AGGCCGGTGCTCCCGATCACGM-3',
SEQ. ID. No.:4; and

Xho-p (internal probe):
5'-TTCGTGGGGTCTGTCGTTCTG-3',
SEQ. ID. No.:5

RNA Expression Analysis

The expression of the transfected Xho-2 or Xho1+2 was investigated using RT-PCR assay. Total RNAs were purified from transfected and control cell pellets using the guanidium isothiocyanate technique (Chomczynski et al., 1987, Anal. Biochem. 162:156–159) and successive extractions with phenouchloroform and chloroform followed by precipitation in 1.5 volume of isopropanol at 4° C. The RNAs pellets were rinsed in 70% ethanol and treated with 100 units of RNase-free DNase1 in the presence of 30 units of RNAguard in a buffer made of 100 mM sodium acetate and 5 mM $MgSO_4$ (pH 5.0) for 5 hours at 25° C. to eliminate residual contaminating DNA. The RNAs samples were further purified by phenol/chloroform/isoamyl alcohol extractions, precipitated in isopropanol, rinsed in 70% ethanol and resuspended in sterile water and stored at −80° C. until used. Five hundred nanograms of extracted RNA were reverse transcribed using reagents and conditions described by Perkin-Elmer and the downstream primer Xho-b. The cDNAs were then amplified with the primers Xho-a and Xho-b, and the PCR products were hybridized with $\alpha^{32}P$-labeled Xho-p probe, as previously described (Guibinga et al., 1996, J. Clin. Microbiol. 34:1654–1659). To control for the specificity of the reaction, RNA samples were similarly amplified but without the reverse transcription step.

Sequence Analysis

The sequence data were obtained by chain terminator sequencing [Sanger et al., 1977, Proc. Natl. Acad. Sci. (USA) 74:5463–5467]. The templates were either pGem-1 or single-stranded Bluescript™ subclones containing Xho-2 subfragments of sizes ranging from 200 bp to 1.3 kb that were obtained after digestion with SmaI or HincII restriction enzymes. Radiolabeled DNA chains were prepared using AMV reverse transcriptase, large fragment of polymerase I or Sequenase™ and $^{35}S$-dATP. To initiate the reactions either primers for promoters harbored by the vectors (Sp6, T7 for pGem-1; T3, T7 for Bluescript™) or synthetic oligonucleotides were used. The reaction products were resolved on 6% polyacrylamide gels. Handling and analysis of the sequence data were made using the Strider program. Searches for homologies of the nucleotide and amino acid sequences were made respectively against the data bank of the Gene Bank and National Biomedical Research Foundation Protein Identification Resource.

Viral Isolates

Undiluted cell culture supernatants of human cytomegalovirus (CMV), varicella-zoster virus (VZV), HSV-1 and HSV-2, isolated from clinical specimens were kept frozen in liquid nitrogen for at most one year. Raji cell line (which contains the Epstein-Barr virus (EBV) genome) and carcinoma cell line HeLa (which contains 40 copies of HPV-18 DNA per cell) were obtained from the American Type and Culture Collection (Rockville, Md., USA). Plasmid pXho 1+2 in the text refers to the Xho-1 and Xho-2 subfragments of BglII N cloned into a pBR322 vector as described by Saavedra et al. (Saavedra et al., 1985, EMBO J. 4:3419–3426). Uninfected human MRC-5 diploid fibroblasts were maintained in Eagle's minimum essential medium supplemented with 10% fetal calf serum.

Clinical Samples

Between January and October 1994, 216 clinical specimens were consecutively obtained from 151 individuals (48 men, 91 women, 12 unknown gender). A total of 137 genital specimens, 71 non-genital specimens, and 8 specimens from unknown sites were obtained. The following sites were sampled: genital lesions (n=128), non-cutaneous and extragenital sites (n=32), cutaneous vesides or ulcers (n=26), perioral and oral lesions (n=13), perianal lesions (n=9), and unidentified origin (n=8). The noncutaneous and extragenital included 27 bronchoalveolar lavages, 3 urine specimens, one eye scraping, and one esophageal brushing. They were selected from stored aliquots kept at −20° C. on the basis of growth in cell culture of herpesviruses other than HSV-2, to evaluate the specificity in vivo of the novel PCR assay. Cutaneous and mucosal specimens were collected on Dacron swabs from lesions in the throat, mouth, genital tract of skin. Swabs were placed immediately in two ml of viral transport medium (Hank's medium supplemented with 1% HERPES, 2% fetal calf serum, 25 pg of vancomycin, 10 µg of tentamicin, and 1.25 µg of amphotericin B) and transported to the laboratory in less than 4 hours. The project had the approval of the Ethics committee of l'Hôpital Notre-Dame, Montréal, Québec, Canada.

Viral Culture

For the preparation of each cell line monolayer, 0.2 ml of a suspension of 500,000 cells per ml of Eagle's minimal essential medium (MEM) containing 10% fetal calf serum was added to each well of a polystyrene microplate (Falcon 3072 Microtest III™ 96-well plate with flat bottom wells; Becton Dickinson, Lincoln Park, N.J.). Plates were incubated at 37° C. in 5% $CO_2$ and confluence generally occurred within three days after inoculation.

For each specimen, fifty µl per well of viral transport medium was inoculated immediately into six wells of a 96-well microtiter plates containing the following monolayer cell lines in duplicate wells: Vero, Mink lung and MRC-5 (diploid human embryonic lung fibroblasts) cell lines. Microplates were centrifuged at 37° C. at 2800 rpm for 30 min (IEC-centra-8R centrifuge, International Equipment company, USA). Two shell vials with MRC-5 cells were also inoculated with 200 µl of viral transport medium per vial. If culture could not be immediately performed, the specimen was kept at 40° C. for at most 18 hours. A portion of the viral transport medium (1,500 µl) was routinely kept at −20° C., until completion of the cell culture, for reinoculation onto cell lines if necessary.

Plates were incubated at 37° C. for 28 days in 5% $CO_2$ and were routinely observed for the presence of cytopathic effect. When a cytopathic effect was observed, HSV was typed with fluorescein-labeled monoclonal antibodies against HSV-1 and HSV-2 specific antigens (Pantho Dx, Diagnostic Products Corporation, Los Angeles, Calif.). Identification was also done by immunofluorescence staining with monoclonal antibodies for VZV (Merifluor VZV, Meridian, Cincinnati, Ohio) and for CMV (gift of clone E-13 from Dr Perrol, Hôpital Saint-Louis, Paris, France).

Treatment of Samples for PCR

Aliquots of specimens in viral transport medium kept at −20° C. were prepared as described in the results section (see below). After processing, the pellet was resuspended in a solution of 20 mM Tris [pH 8.3]. Samples were lysed by addition of Tween 20™ [final concentration of 0.4% (v/v)] and Nodidet P40™ [final concentration of 0.4% (v/v)], and digested, for 2 h at 60° C. with proteinase K at a final concentration of 250 µg/ml. Cell lysates were denatured at 95° C. for 10 min and stored at −70° C. until tested with PCR.

Genomic Amplification for HSV-2 (Xho-2 PCR)

Samples were tested with PCR without the knowledge of culture results. Ten µl of each sample lysate was added to 90 µl of a PCR reaction mixture containing (final concentrations) 10 mM Tris [pH 8.3], 50 mM KCl, 2.5 mM MgC12 (Gene Amp PCR buffer II from Perkin Elmer Cetus, Montreal, Que., Canada), 50 pmol each of Xho-a and -b, 200 µM of each deoxynucleoside triphosphates (dATP, dCTP, dGTP, and dTTP) and 2.5 units of Thermus aquaticus (Taq) DNA polymerase (Roche Molecular Diagnostics, Mississauga, Ont., Canada). Samples were overlaid with 100 µl of mineral oil and amplified in a 480 DNA thermal cycler heat block instrument (Perkin-Elmer Cetus) through 35 cycles of denaturation at 94° C. for 1 min, primer reannealing at 60° C. for 1 min and primer extension at 72° C. for 1 min. In each run, a buffer negative control and ten copies of the plasmid pXho1+2, were included. A run was discarded if one of the negative controls tested positive, or if the ten-copy positive control scored negative. Discordant results between culture and Xho-2 PCR were resolved by supplementary testing: samples were retested in duplicates with Xho-2 PCR, were amplified for β-globin with PC04/GH20 primers (2), and tested in a standard PCR test for detection of sequences from the DNA polymerase gene of HSV-2 (Nahass et al., 1992, JAMA 268:2541–44) with primers HCJ3/HCJ12 and probe HCJ6.

Measures to avoid false-positive reactions due to contamination included the use of disposable pipettors for initial processing of clinical samples or isolates, performance of each step of PCR in different areas of the laboratory, use of filter pipette tips (USA Scientific Plastics Inc., Ocala, Fla.), aliquoting PCR reagents, inclusion of multiple negative controls per run, and meticulous laboratory procedures. Pipettors for pre-PCR manipulations were used solely for this purpose.

Detection of HSV-2 DNA Amplified Products

Confirmation of the specific amplification of Xho-2 sequences was obtained by hybridization of amplified products with an internal oligonucleotide in a dot blot assay. Ten µl of amplified products was mixed with 100 µl of denaturing solution composed of 0.4 N sodium hydroxyde and 25 mmol/L EDTA, and applied to replicate nylon membranes. Filters were prehybridized at 62° C. for 30 min in 6×SSC (1×SSC is 0.15 sodium chloride and 0.015 M sodium citrate [pH 7.0]), 5×Denhart's, 0.1% sodium dodecyl sulfate and 100 mg per ml of denatured salmon sperm DNA Internal probe Xhop end-labeled with $^{32}$P-ATP was added at 150,000 cpm per ml of hybridization buffer. Hybridization was performed for 90 min at 62° C. Blots were washed twice for 15 min at 62° C. in 2×SSC and 0.1% SDS. Autoradiograph exposures were obtained 16 hours after hybridization.

Statistical Analysis

The sensitivity and specificity of Xho-2 PCR were first calculated considering culture as the gold standard. The crude percentage agreement between both detection methods was the percentage of samples where results were identical. The kappa statistic's was calculated to adjust for chance agreement between detection methods (4). In general, a kappa value above 0.75 represents excellent agreement beyond chance.

2—RESULTS

Derivation of HSV-2 Cervical Cell Lines

To define the copathogenic transforming activity of BglII N in greater detail, the effect of two of its subfragments Xho-2 and Xho1+2 (Saavedra et al., 1985, EMBO J. 4:3419–3426) was determined in normal and HPV-16 or –18 immortalized genital epithelial cells. After cotransfection with MDR resistance gene and pXhoI or pXho1+2 plasmids the cultures were maintained in selective medium containing 10 ng/ml$^{-1}$ colchicine; after ten days most cells died, but a few resistant colonies did develop. Normal genital epithelial cells were not immortalized by the pXho-2 or pXho1+2 subfragments. Colonies observed with pHaMDR treatment only and those obtained with the pXho-2 or pXho1+2, plus the pHaMDR, were indistinguishable. When the cultures became confluent, each dish was trypsinized and split into 2 dishes and grown as mass (M) cultures. In some cases, colonies were isolated with cloning pipettes. These cells were then transferred to a one-well of a 24-well plate, grown to confluency, and eventually transferred to a 100 ml plastic dish. These were identified as clones (C). The cell lines which had been propagated in MCDB-153-LB were switched to MCDB-153-LB lacking bovine pituitary extract plus 5 percent fetal bovine serum when about 50 percent confluent after the tenth subpassage. Some cells differentiated in the presence of serum; however, after an additional 3 to 5 passages, the cells formed colonies indistinguishable from one another, independent of whether they had been treated with the colchicine resistant gene only or with pXho1+2 of pXho-2 and the colchicine resistant gene. Subsequently, the cultures were split 1 to 10 every 7 to 10 days. A total of 30 cell lines which had been transfected with pXho-2 or pXho1+2 were established; their growth rate was independent of whether the line was derived from a done or mass culture.

HSV-2 DNA Detection in the Transfected Cell Lines and Derived Tumors

Cultures derived from transfection of HPVGS, CX16-1, CX16-5 and CX18-1 cell lines with pXho1+2, pXho-2 or control pHC79 plasmids were examined for the presence of the viral sequences by Southern blot analysis The cellular DNAs were digested with BamHI and probed with $^{32}$P-labeled Xho-2. Because one BamHI restriction site is present in Xho1, this enzyme was used for DNA digestion to ascertain the integrity of the Xho-2 fragment in the transfected cells. With these conditions, the inserts in the transfected cells should resolve in bands larger than 2.4 kb, the size of Xho-2. A positive signal for Xho-2 sequences was observed in 17 of 26 cell lines. The presence of Xho-2 sequences was detected in one of the CX18-1 transfectants (Xho1+2:2M), five of seven CX16-5 lines (CX16-5-Xho-2:2C, -Xho1+2:1M, -Xho1+2:2M, -Xho1+2:1C, -Xho1+2:2C), six of 13 CX16-2 lines (CX16-2-Xho-2:3C, -Xho-2:1M, -Xho1+2:1M, -Xho1+2:1C, -Xho1+2:3C, -Xho1+2:4C) and two of four HPVGS (HPGS-Xho1+2:C and -Xho1+2:3C). As expected, the bands were all above the size of the control Xho-2 segment, thus indicating that at least the Xho-2 sequences were integrally retained in all the positive transfectants. This signal was specific and never detected in cells not previously transfected with Xho plasmids. Furthermore, the reexamination of these cell lines at higher passage demonstrated the persistence of the Xho-2 fragment.

Four representative cell lines originating from the different parental cell lines and harboring either Xho-2 or Xho1+2 sequences were assayed for tumorigenicity using subcutaneous injections of $5 \times 10^6$ to $1 \times 10^7$ cells in SCID or Beige mice. All the tested cell lines (HPVGS-Xho-2:1M, CX16-2-Xho1+2:3C, CX16-5-Xho1+2:2C and CX18-1 -Xho1+2:2C) produced tumors by four weeks post injection, as assessed by histology of the tumors under 250 or 400 times magnification. The carcinomas exhibited indolent in their growth and were diagnosed as being invasive (CX18-1 -Xho1+2:2C) and non-invasive and well differentiated cystic squamous carcinomas (CX16-2-Xho1+2:3C). The same cell lines transfected with the control plasmid pHC79 never demonstrated the tumorigenic phenotype.

To ascertain that the tumors derived from the injected cells, the DNA extracted from paraffin sections of each tumor was amplified using the primers and probe specific for Xho-2. All tumors demonstrated the amplified fragment of 200 bp characteristic of Xho-2 sequence, in EtBr stained gel or after hybridization with the Xho-p probe (SEQ. ID No:5). These data confirm that the tumors developed in host animals derived from the injected cell lines. In addition, they also show that Xho-2 alone could induce the tumorigenic conversion of the HPV-immortalized cervical cell lines, as it was already observed with NIH3T3 cells (Saavedra et al., 1985, EMBO J. 4:3419–3426).

Sequence Analysis of HSV-2 BglII N Xho-2 Subfragment

Since Xho-2 sequences were found sufficient enough to induce the tumorigenic conversion, its sequence was determined. The complete sequence between Xho1 and BglII sites is 2469 base pairs (bp) long. The G+C content of 71.4% is slightly higher than the 68.6% of the neighboring glycoprotein C sequence or the 68% of the left end portion of the BglII N fragment (Galloway et al., 1984, J. Virol. 49:724–730). The sequence (FIG. 8 and SEQ. ID. No.:1) shows the presence of a palindrome extending over 100 bp between the nucleotides 1391–1490 which is capable of forming a stem loop structure with a free energy equivalent to –76.4 Kcal. The search for nucleotide sequence homologies against GenBank data base revealed several sequences with significant percentages of similarity. The portion of the Xho-2 segment between the HincII and the 3' end BglII sites has been sequenced (Swain et al., 1985, J. Virol. 53:561–569); the nucleotide chains in both analyses were found in full agreement as both derive from strain 333 of HSV-2. This analysis revealed a region showing 75% homology with ORF-UL43 which maps collinearly to Xho-2 in HSV-1 (McGeoch et al., 1988, J. Virol. 69:1531–1574). Finally, the other sequences that showed some homology include limited stretches of nucleotides from genes or segments of HSV-1 and HSV-2 viruses, (HSV-1 glycoprotein C, HSV-1 and 2 L-S inversion), EBV, pseudorabies, human PDGF-A, mouse androgen regulated RP2 and mouse N-myc protooncogene). The search for ORFs within the Xho-2 segment showed, between the nucleotides 559 and 1794, the presence of a sense open reading frame (Xho-2-ORF) predicted to encode a protein of 413 residues with a predicted molecular weight of 42–43 kD. The TATA box and polyadenylation signals for the ORF are respectively located between nucleotides 495–500 and 1808–1815. A CCAAT sequence that might represent a CAT box is located at nucleotides 411–415. Interestingly, the antisense ORF, homologous to the UL43.5 ORF recently described by Ward et al. (Ward et al., 1996, Journal of Virology 70:2684–2690) in HSV-1, was not found within the boundaries of this Xho-2-ORF. Also, as noted in HSV-1 (Ward et al., 1996, Journal of Virology 70:2684–2690), a putative antisense ORF lying between nucleotides 2099 and 1481 was noticed; however, no appropriate TATA box or polyadenylation signal were observed, whether this antisense ORF truly exists remains to be determined. Finally, the right end portion of Xho-2 segment contains the N-terminus of the gC-2 gene The amino acid sequence predicted from the Xho-2ORF was compared with the protein library of the National Biomedical Research Foundation. As expected from the nucleotide sequence, the most extensive homology (66%) was with the HSV-1 UL43 protein (433aa), suggesting that both proteins belong to the same family. This was further supported by their respective hydrophobic/hydrophilic profiles which exhibited several possible membrane-spanning sections usually observed in membrane-associated proteins. There was also homology with segments from the following proteins: the 70.5 Kd trans-inducing protein of HSV-1 (38.7%), $E.coli$ t-RNA synthetase (51.3%), collagen family (29 to 33%), HSV-1 immediate early proteins IE110 and IE175. Interestingly, most of the homologies with HSV proteins are clustered within the NH2 terminal portion of the predicted Xho-2 protein. Concerning the putative antisense ORF present in Xho-2 segment, the protein analysis revealed no significant homology with any of the proteins in the data bank; the only homologies found were with limited segments of the collagen genes family. Taken together with the lack of a classical transcription signals and the absence of a corresponding transcript which would have mapped within the BglII N fragment (Jenkins et al., 1984, J. Virol. 52:99–107), these data shed doubts about the true existence of such an antisense ORF. Nevertheless, based on the presence thereof in HSV-1, these data validate the potential of an antisense therapy.

Xho-2 RNA Expression

Since a Xho-2-ORF was present in the Xho-2 segment, the expression of the corresponding mRNA was investigated in four cell lines, the same that were tested for tumor formation. This was done using RT-PCR with primers selected within the ORF sequence and which demonstrated a high specificity for the HSV-2 Xho-2 subfragment (Guibinga et al., 1995, Arch. STD/HIV Res. 9:163–179.). The RNAs were purified from CX16-2 Xho1+2:3C, CX16-5 Xho1+2:2C and CX18-1 Xho1+2:2C and HPVGS Xho-2:1M and the non transfected CX16-2. The RT-PCR amplified products were analysed by performing electrophoresis on a 2% agarose gel, transfering onto a nylon membrane and hybridizing with the Xho-p internal probe. RNA expression was detected in CX16-2:3C and CX16-5:2C cells, HPVGS 1M but not in CX18-1:2C. The control for the amplification reaction, using HSV-2 DNA as template, gave the expected band. The negative controls, including RT-PCR reactions on non-transfected CX16-2 RNAs and RNAs from test samples, but without the reverse transcription step (CX12-5:2C, no RT), were all negative. These results show that CX16-2:3C, CX16-5:2C and HPVGS:1M cells express mRNA transcribed from the Xho-2 segment.

Optimization of HSV-2 PCR

Xho-2 is a 2.480 kb fragment with a G+C content of 71.4%. Primer sequences were selected within the predicted open reading frame (ORF) of Xho-2 located between nucleotides 559 and 1797. We avoided GC stretches and nucleotide positions within a palindromic sequence located between bp 1391–1490 of the sequenced fragment and forming a stem loop structure. The primers selected, Xho-a and -b, did not form primer dimers, had a similar G+C content and did not contain repetitve sequences. The primer and probe sequences were unique to HSV-2 by comparison with all human, viral and bacterial sequences in the data base Genbank (Los Alamos National Laboratories) by alignment using the BLAST sequence analysis software (1) from the Genetic Computer Group. Xho-a and -b defined a 189 pb DNA fragment from HSV-2.

The various parameters of PCR were first optimized by amplifying 10,000 copies of pXho-1+2. Amplification products were migrated on an agarose gel and stained with ethidium bromide. The intensity of the bands generated through the different PCR conditions were compared. A Hot-Start PCR technique at 75° C. did not alter the specificity and sensitivity of detection of HSV-2 DNA template (data not shown). While the efficiency of amplification was reduced for concentrations of $MgCl_2$ below 2 mM, no difference was recorded for concentrations ranging from 2 to 4 mM (data not shown). The $MgCl_2$ concentration was adjusted to 2.5 mM for all other experiments.

Figure 2:
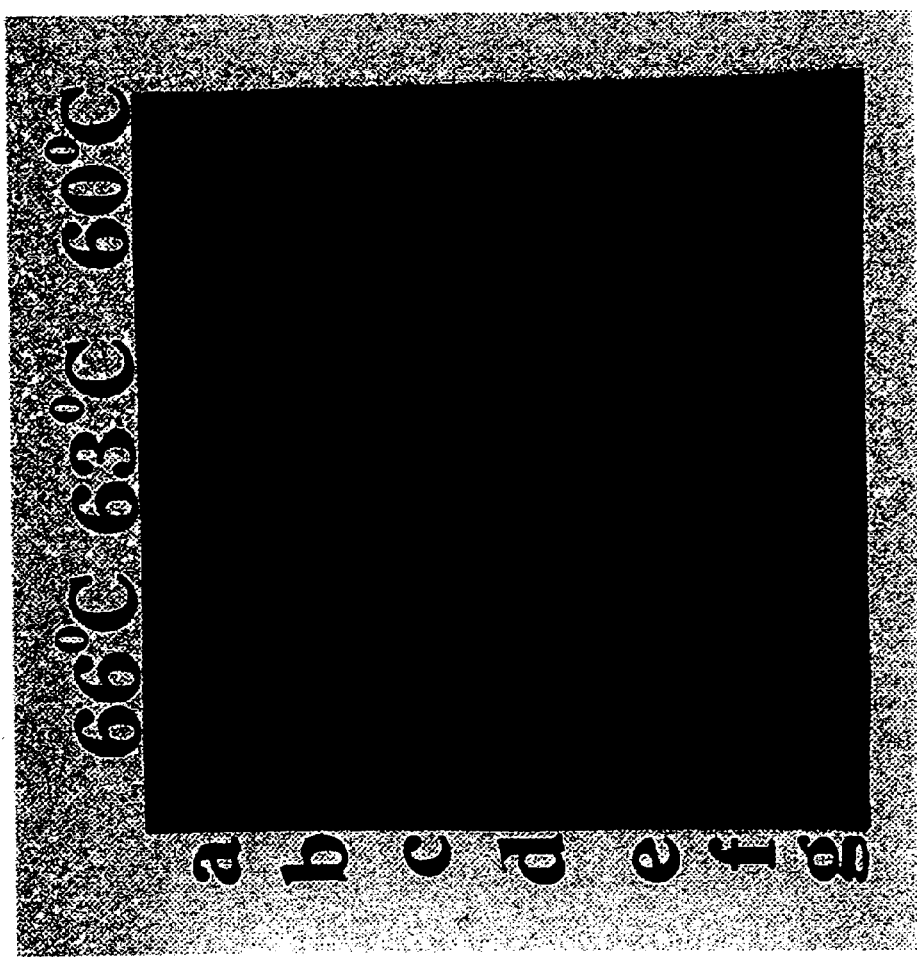
FIG. 2 shows the influence of the primer reannealing temperature on the efficiency of Xho-2 PCR to detect HSV-2 DNA. Serial five-fold dilutions of pXho-1+2 (line a: 15,625 copies; b: 3,125 copies; c: 625 copies; d: 25 copies; e: 5 copies; f: 1 copy; and g: 0 copy) were amplified with Xho-2 PCR under different primer reannealing temperatures (66° C., 63° C. and 60° C.), and hybridized with radiolabeled Xho-p.

Because of the high G+C content of the Xho-2, improvement in the sensitivity of the Xho-2 PCR test was tried by increasing the length of the denaturation step to 2 minutes. The increase in denaturation time resulted in increased signals for HSV-2 DNA detection as shown in FIG. 1. The influence of the reannealing temperature on the performance of PCR to detect HSV-2 DNA was then studied. Fivefold dilutions of pXho-1+2 were amplified under various reannealing temperatures, analyzed by gel electrophoresis and reacted with the internal probe at 62° C. Temperatures above 60° C. generated less intense non-specific bands on ethidium bromide stained gels of PCR products from herpesviruses other than HSV-2 (data not shown). A loss in sensitivity was encountered with reannealing temperature above 60° C. (FIG. 2). At 60° C., a very low level of background reactivity was inconsistently observed. This background reactivity was similar to that of the negative control using the usual master mix but without Taq polymerase (data not shown). This background reactivity when present was always weak and much lower than the 10 HSV-2 DNA copy control (data not shown).

in Vitro Sensitivity of Xho-2 PCR for Detection of HSV-2 DNA

To estimate the sensitivity of the PCR assay for detection of Xho-2 DNA, serial fivefold dilutions of pXho-1+2 were prepared and each dilution was tested for the presence of Xho-2 DNA using PCR and hybridization with internal probe. Results are presented in FIG. 2. The assay could detect one copy of pXho-1+2 DNA. Using DNA extracted from HSV-2, we reached a similar endpoint (data not shown).

Specificity of Xho-2 PCR

Figure 3:
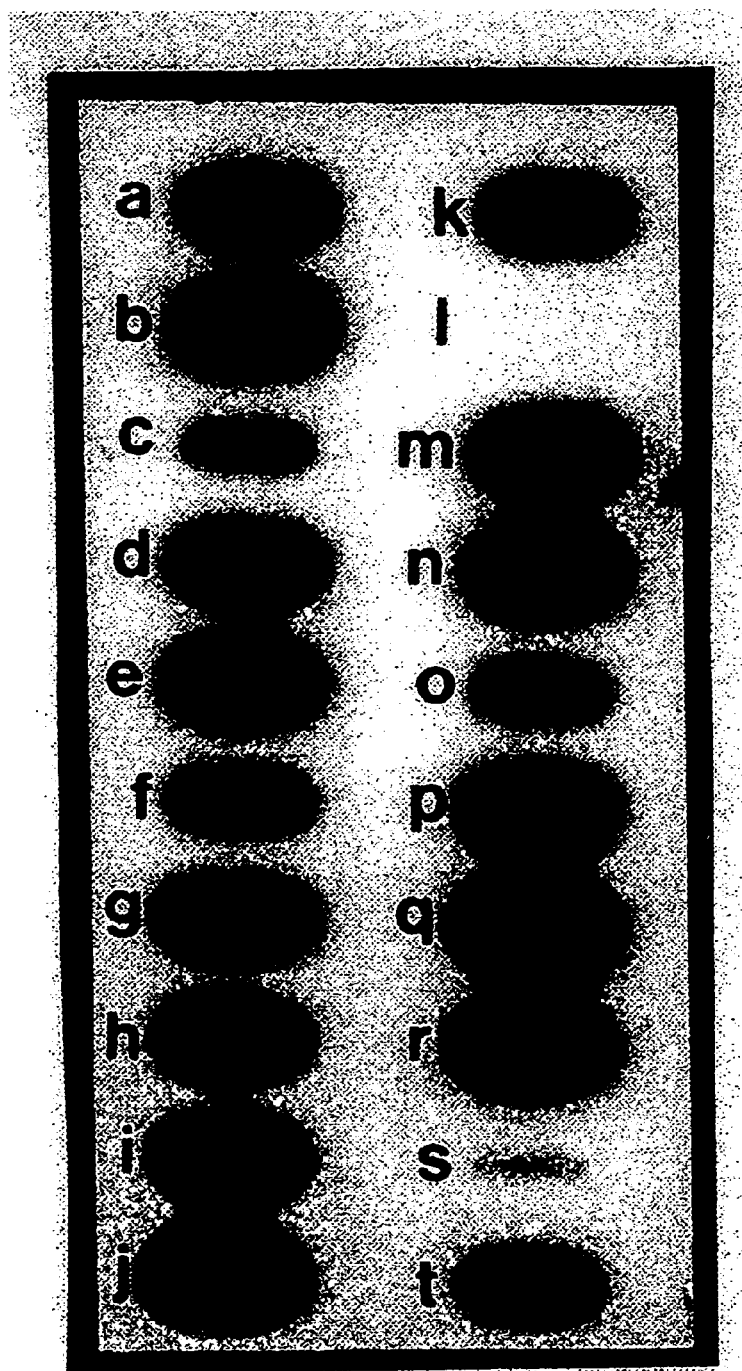
FIG. 3 shows the detection of various HSV-2 isolates with Xho-2 PCR. Various cell culture supernatants from which HSV-2 had been grown (a-k, m-r), were treated and amplified as taught herein in Materials and Methods section. t is a positive control from a cell culture supernatant containing HSV-2. s is the 10 copy control of pXho-1+2, and I is the blank negative control (buffer control)

To determine if primer and probe sequences were conserved amongst HSV-2, 43 HSV-2 isolates from undiluted cell culture supernatants kept frozen in liquid nitrogen, were lysed and tested with PCR. Viral isolates came from different individuals. All yielded a specific 189-bp band and reacted with the internal probe in the dot blot assay (see FIG. 3).

Figure 4:
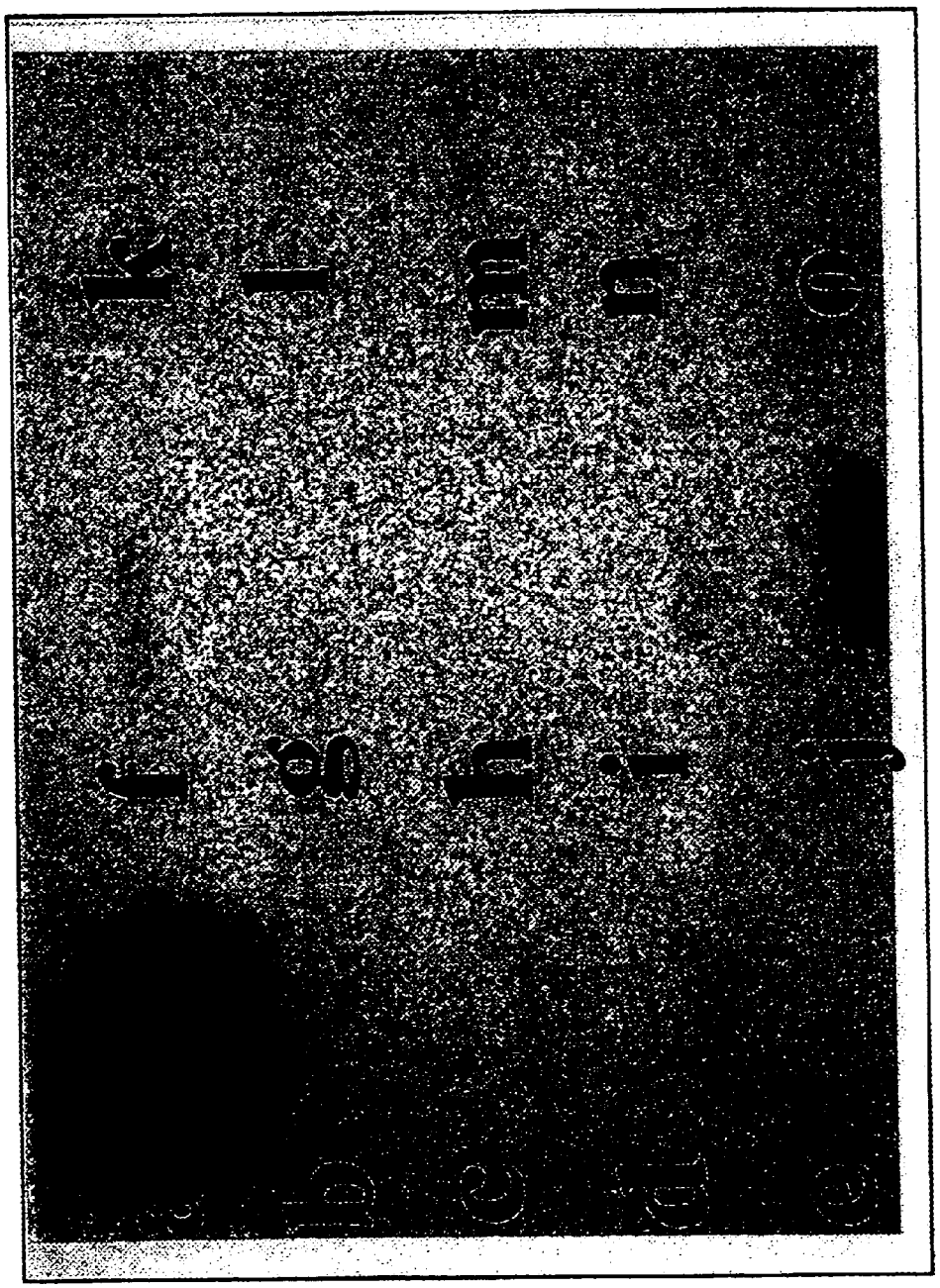
FIG. 4 demonstrates the specificity of the Xho-2 PCR test for HSV-2 detection. Cell culture supernatants were treated and amplified according to the Materials and Methods section. Isolates tested were CMV (b,c,d), HSV-I (e,f,g,h), VZV (i,k). One µg of extracted DNA from Raji cells were also tested (I), as well as one ng of HPV-16 (m), and 100,000 lysed PBMCs (n). a is the strong positive control from a cell culture supernatant of an HSV-2 positive sample. j is the 10 copy control of pXho-1+2, and o is the blank negative control (buffer control)

To confirm that the primers and probe selected were specific for HSV-2 sequences, isolates of herpesviruses other than HSV-2 from different individuals were analyzed with PCR. Undiluted cell culture supernatants kept frozen in liquid nitrogen were lysed and tested for the presence of HSV-2 Xho-2 DNA using the Xho-2 PCR assay. The specificity of PCR was evaluated on 10 CMV isolates, 11 VZV isolates, 18 HSV-I isolates, and one pg of DNA exacted from Raji cells (FIG. 4). One ng of HIV-1 proviral DNA contained in pSP64, human DNA from 100,000 lysed peripheral blood mononuclear cells (PBMCs), one ng of plasmid vectors containing HPV DNA inserts of types 6, 11, 16, 18, 31, 33, 35 and 45 were also analyzed. After amplification of these various templates with Mesa and Xhob primers, no specific DNA product could be identified by hybridization with Xho-p.

Treatment of Clinical Samples

Figure 5:
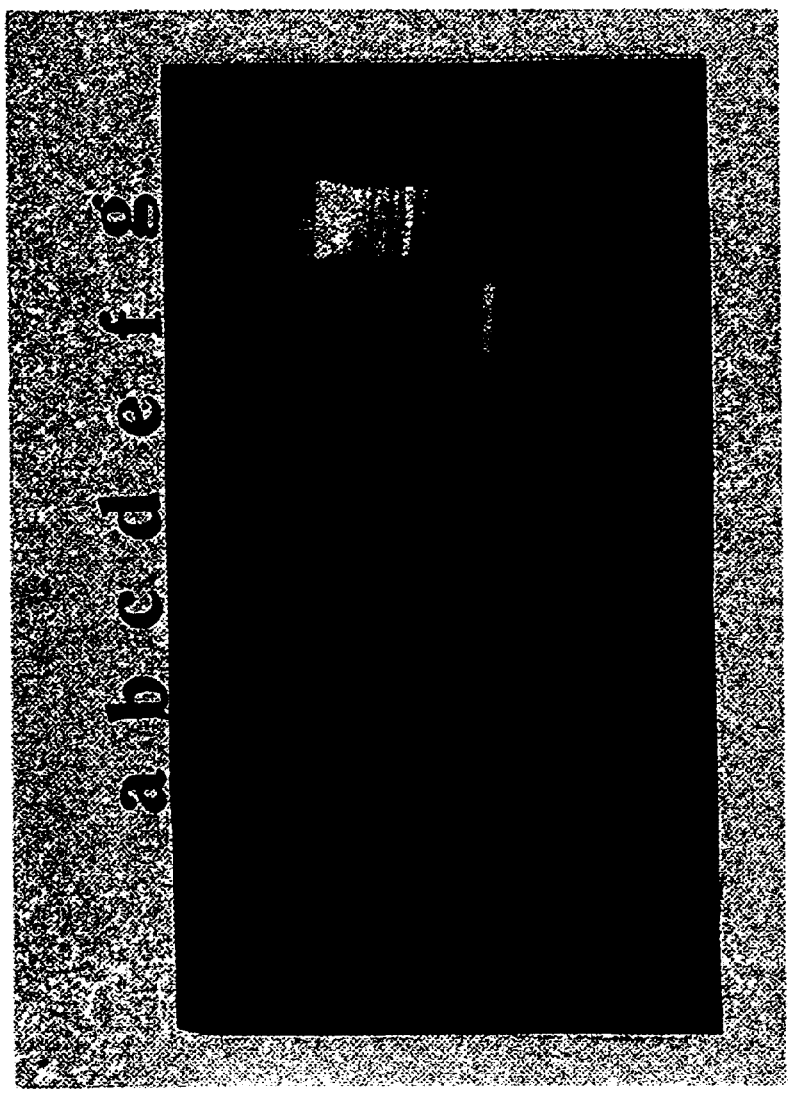
FIG. 5 shows the influence of the viral transport medium protocol on the ability of Xho-2 PCR to detect HSV-2 in clinical specimens. A pool of specimens infected with HSV-2 was treated with various specimen preparations, amplified with Xho-2 PCR and migrated on a 2% agarose gel stained with ethidium bromide. a is the negative control, b is treatment protocol one in which specimens in viral transport medium were centrifuged at 13,000 rpm for 10 min in a microfuge, lysed with detergents and proteinase K c is the second specimen treatment protocol in which viral transport medium was lysed with detergents and proteinase, purified with two phenol-chloroform extractions, and precipitated with ethanol before amplification, d is the third protocol in which viral transport medium was lysed with detergent and proteinase and amplified. e is the negative buffer control and f is the positive pXho-1+2 control. g is a 100 bp ladder.

The optimal processing protocol of clinical specimens contained in viral transport medium for PCR was determined by comparing three sample preparation methods. Three samples contained in viral transport medium that had been positive by culture for HSV-2, were freeze-thawed, pooled and treated as follows. In the first method, 300 µl of the pooled specimens in viral transport medium was centrifuged at 13,000 rpm for 10 minutes in a microfuge (Eppendorf™ minifuge). The pellet was resuspended in 100 µl of 10 mM Tris [pH 7.0] and 0.1 mM EDTA (TE), and lysed with detergents and proteinase K at 60° C. for 2 h as described in the Materials and Methods section. After denaturation at 95° C. for ten min, ten µl of lysate was added to the PCR master mix and amplified according to the standard procedure. In the second specimen treatment protocol, 300 µl of specimen in viral transport medium was lysed with detergents and proteinase K at 60° C. for 2 h, and denatured at 95° C. for 10 min. DNA was then purified with two phenol/chloroform extractions, and precipitated with ethanol. The pellet was resuspended in 30 µl of TE of which ten µl was amplified with PCR. In the third protocol, 300 µl of the specimen in viral transport medium was lysed as above at 60° C. for 2 h and denatured at 95° C. for 10 min. Ten µl of the lysate was then added directly to the PCR mixture and amplified. Products of amplification from each protocol were then migrated on a 2% agarose gel stained with ethidium bromide. As shown in FIG. 5, specimen preparation according to protocol one was more efficient than the other protocols. This protocol was selected for the comparison of cell culture and Xho-2 PCR on clinical specimens.

Performance of PCR on Clinical Samples

A total of 176 frozen specimens sampled from cutaneous and mucosal sites, that had been cultivated for HSV before freezing, were randomly retrieved and processed for PCR using the specimen treatment protocol one. Thirty-two specimens from non-cutaneous extra-genital sites were also included to evaluate cross-reactivity of Xho-2 PCR with other herpesviruses isolated from these clinical specimens. Eight specimens from unknown sites were also obtained. All samples in viral transport medium had been collected prospectively and kept frozen at −20° C. after inoculation of cell culture. The presence of HSV-2 DNA was assessed by dot-bloting PCR-amplified products and probed with the radiolabeled Xhop probe. Since 50 µl per well of viral transport medium were inoculated into six wells containing various cell lines, a total of 300 µl of the viral transport medium was tested in cell culture. The same quantity of viral transport medium was processed for PCR but only one tenth was introduced in each PCR run. Of the 151 participating individuals, 127 provided one sample and 24 patients provided more than one specimen. An average of 1.43±1.62 specimens per patient was tested (range of the number of specimen tested per patient, 1–15).

Figure 6A:
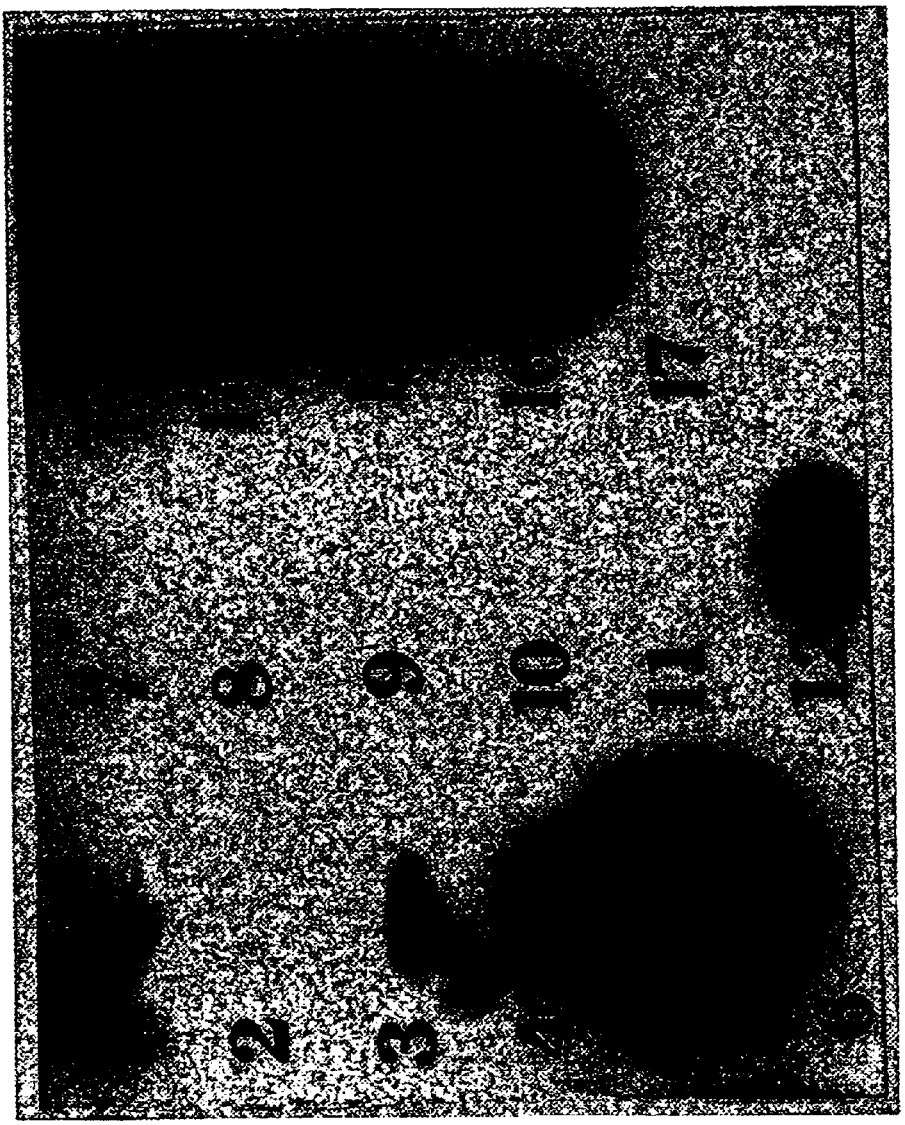
FIG. 6 shows the detection of Xho-2 DNA in clinical specimens. Samples were treated and amplified with Xho-2 PCR as described in the Materials and Methods section. In A, specimens 1, 2, 7–11, 17 were negative for HSV-2 by PCR and culture while specimens 3, 4, 5, 13–16 were positive in both tests. 12 is the 10 copy control of pXho-1+2, and 6 is the negative control. In B, serial specimens from the same individual were tested with PCR and culture. Specimen 1, 5, 6 were positive in culture and PCR while specimens 3 and 4 were negative in both tests. Specimen 2 was negative in culture but positive with PCR, and was sampled one day after sample 1.
Figure 6B:
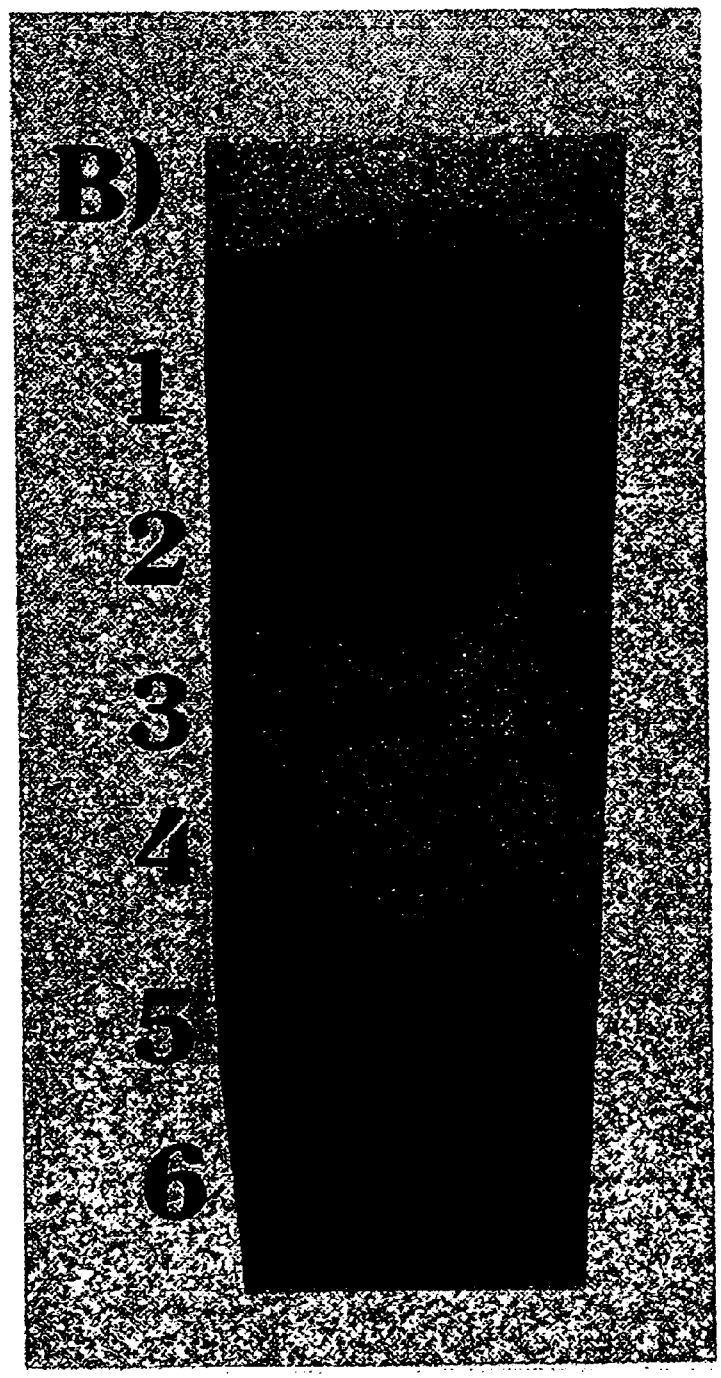
Figure 7:
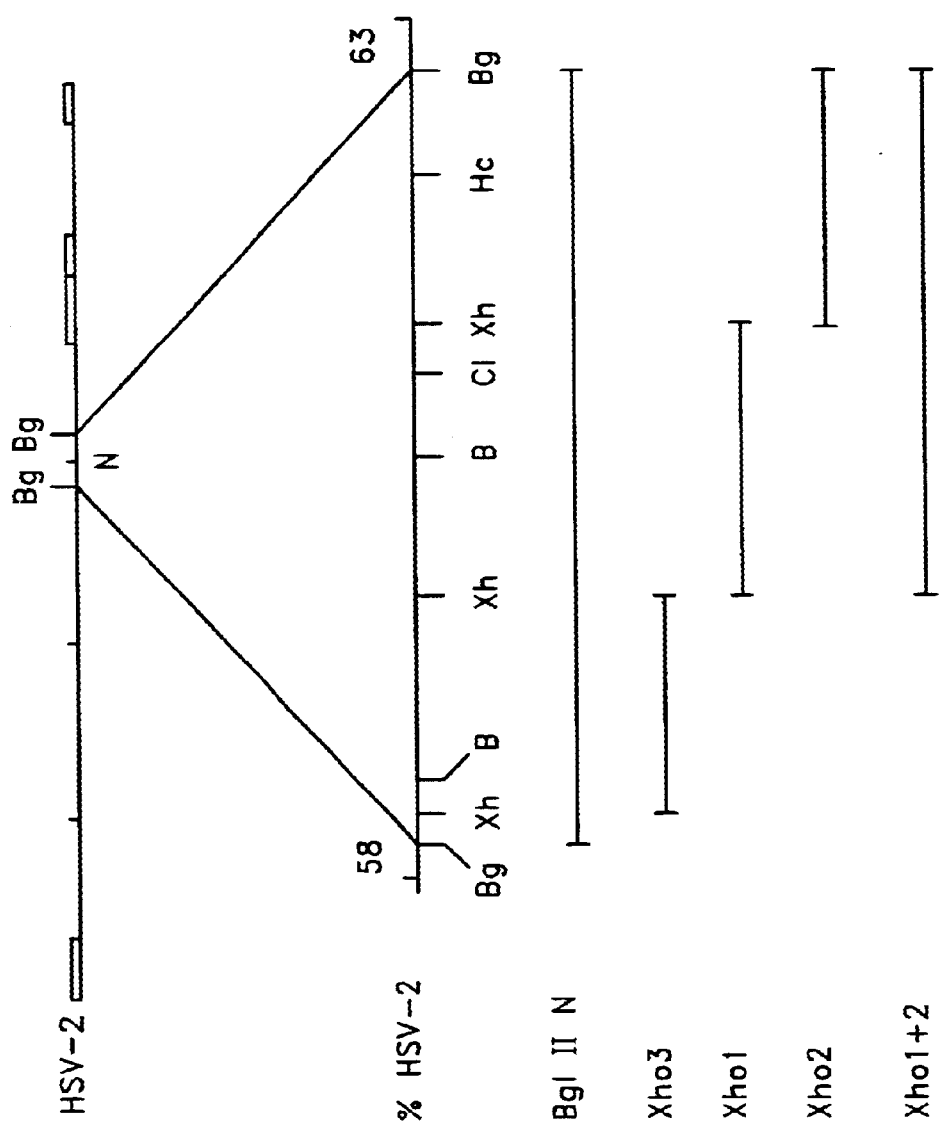
FIG. 7 shows the physical map of HSV-2 BglII N fragment and its Xho-1 subfragments; Restriction enzymes are:Bg:BglII N; Xh: XhoI; Cl: Cla I.

Overall, viral sequences were detected in 107 (49.5%) out of 216 specimens (FIG. 6A). Xho-2 DNA sequences were detected in 105 (sensitivity of 98.1%) of 107 specimens with culture-proven HSV-2 infections. Both tests were negative for HSV-2 in 107 specimens and both were positive in 105 samples tested, for a concordance between these methods of 98.1% (212 out of 216 samples) and a near perfect kappa value of 0.96. Cell culture was negative for HSV-2 for 109 samples, of which CMV was isolated in 15, VZV in 5 and HSV-I in 22 samples. Two of the culture-negative specimens contained HSV-2 DNA sequences by the Xho-2 PCR assay, for a specificity of 98.3% (FIG. 6B).

Evaluation of Discordant Specimens

Xho-2 PCR and cell culture provided discrepant results on four specimens. We investigated the discrepant test results by retesting in duplicates specimen lysates with the Xho-2 PCR test, with a standard HSV-2 PCR test for the DNA polymerase gene (Nahass et al., 1992, JAMA 268:2541–44), and with a β-globin PCR test. Both of the PCR-positive culture-negative specimens scored positive in the HSV-2 DNA polymerase and Xho-2 PCR assays. One of these individuals had applied topical acyclovir on the lesion while the other one was receiving oral acyclovir. Both had previous samples positive in culture and PCR for HSV-2 the day before the PCR-positive culture-negative specimen was sampled (see FIG. 6B). They were thus considered true positives for HSV-2. One of the two falsely-negative Xho-2 PCR specimens was indeterminate in duplicate testings with Xho-2 PCR (one positive and one negative reaction). Positive results were obtained for β-globin and HSV-2 DNA polymerase sequences for the latter. The other Xho-2 PCR-negative sample tested negative for β-globin and HSV-2 DNA polymerase sequences, suggesting that this specimen may have been inadequate for PCR analysis. Dilution of the β-globin negative sample did not improve results obtained with the PCR assays. The HSV-2 isolates from cell culture supernatants from both patients were amplified with Xho-2 PCR.

The sensitivity and specificity of each technique was recalculated using an extended gold standard definition of HSV-2 infection (see Materials and Methods section). Overall, culture and PCR were each positive for 107 (98.3%) of 109 cases of HSV-2 infections. The specificity of PCR reached 100%.

3—DISCUSSION

There is compelling evidence linking HPV to the etiology of squamous cell carcinomas; however it is also well accepted that additional factors, endogenous or exogenous, are necessary for the apparition of the tumors. HSV-2 infection is one of the oncogenic cofactors that was mostly evoked in cervical cancer, although its role has not yet been clearly established. This study provides the first evidence that a subfragment of HSV-2 BglII N is capable of inducing the tumorigenic conversion of human genital epithelial cells first immortalized by HPV-16 or 18. The same HPV immortalized lines without the addition of the Xho-2 or Xho1+2 failed to produce tumors; these data further support other observations that high risk HPV types are not sufficient for the apparition of cervical cancers. Of importance also is the retention of the Xho segments in 17 transfected cell lines and the tumors that were derived. These results extend our previous observations showing that: i) BglII N, when transfected in its entirety in NIH3T3 (Saavedra et al., 1985, EMBO J. 4:3419–3426) or human genital keratinocytes (DiPaolo et al., 1990, Virology 177:777–779) is not retained whereas its XhoI restricted subfragments are maintained in these cells. It was hypothesized that BglII N could be toxic when present in too high copy number or because of simultaneous expression of the proteins it encodes; this toxicity is abolished when BglII N subfragments are-used (Saavedra et al., 1985, EMBO J. 4:3419–3426). ii) As in NIH3T3 (Saavedra et al., 1985, EMBO J. 4:3419–3426), Xho-2, the smallest of the two subfragments tested, produced the tumorigenic conversion in HPV immortalized cell lines. This suggests, that this segment, harbors an oncogenic function that cooperates with or complements the immortalization inducing genes in these cell lines. iii) The sequence analysis of Xho-2 segment revealed an ORF which is the homolog of UL43 in HSV-1. Interestingly, three of the four representative cell lines that were analysed demonstrated mRNA expression of this ORF. This data argues favorably for a positive correlation between the retention and expression of Xho-2-ORF and the tumorigenic conversion of the HPV immortalized cells. The lack of expression in one of these cell lines could be due to undetectable amount of Xho-2-ORF mRNA or to rearrangements in its sequence; in this case, the tumorigenic conversion might have resulted from integration of the transfected sequences in critical sites of the host genome, a mechanism that could never be ruled out when using a transfection approach. Without being linked by a particular mechanism, the present invention clearly shows that Xho-2 is sufficient to promote tumorigenic conversion in cells.

The nucleotide sequence of Xho-2 and its predicted protein demonstrated a very high percentage of homology with the UL43 of HSV-1. This was not surprising since both subtypes are collinear in most of their genome. Both proteins share similar hydrophobic/hydrophilic profiles which showed several possible membrane-spanning sections usually observed in transmembrane proteins and thus, both could represent members of the same gene family. This similarity extends beyond UL43 and Xho-2-ORF as almost all the transcripts that were mapped in the HSV-1 BamHI fragment, including the putative antisense ORF between UL43 and UL44, have their homologs at a similar position in HSV-2. However, some differences were observed. i) Structurally, the most notable change is the absence of an antisense ORF with size and characteristics of UL43.5. This antisense was found missing in several other herpes viruses (Ward et al., 1996, Journal of Virology 70:2684–2690) and HSV-2 is no exception. This is rather striking when considering the collinearity in the organization of the two subtype genomes. As a consequence, the expression of Xho-2-ORF is expected not to be influenced by the antisense transcription mechanism (Carter et al., 1996, J. Virol. 70:7663–7668). In addition, the alignment of the amino-acid sequences of UL43 and predicted Xho-2 proteins showed less homology within the 25 first residues; this allowed us to develop a PCR test specific for Xho-2 subfragment which proved very useful not only for the detection of the encoded mRNA but also for virus subtyping in clinical specimens (Guibinga et al., 1996, J. Clin. Microbiol. 34:1654–1659). Other primers in the Xho-2-ORF were not discriminant between the two subtypes. ii) At the biological level, the transforming potential associated with BglII N or its Xho subfragments was not found for HSV-1 BamHI segment (Reyes et al., 1979, Cold Spring Harbor Symp. Quant. Biol. 44:629–641). When comparing this segment with its equivalent in HSV-2 the only apparent difference is the absence of the homolog of the UL43.5 antisense gene. As already mentioned this probably would lead to a relatively higher level of expression of the transcripts. But would this difference in expression level of Xho-2-ORF be enough to account for the transforming potential of the Xho-2 segment?

The expression of an HSV-2 Xho-2 specific antisense, an engineered homolog of UL43.5, could thus reduce the expression of Xho-2 ORF and possibly compromise the tumorigenic promotion potential of Xho-2. The present invention provides means to design and test this likely possibility.

The characterization of the UL43 protein by Carter et al. (Carter et al., 1996, J. Virol. 70:7663–7668) revealed a protein with several membrane spanning sections which is apparently smaller than expected from its transcript. It has several membrane spanning sections similar to those found in membrane channel proteins. It was then proposed that UL43 could be a membrane channel protein. Although not yet characterized, the protein predicted from the Xho-2 ORF appears structurally very similar to UL43 and thus could also be a transmembrane protein. It is noteworthy that several transmembrane proteins have been implicated in oncogenic transformation.

The present study demonstrated that HSV-2 Xho-2 DNA sequences could be detected in vitro and in clinical specimens using PCR, even in culture negative samples. Type-specific PCR assays using probes, restriction endonuclease cleavage or nonisotopic hybridization had already been described for the detection and typing of HSV in clinical specimens. Most of these assays focused on the DNA polymerase gene. Herein, only HSV-2 was detected and typed, since the aim was to develop and validate a method for HSV-2 transforming sequences detection and to evaluate their role in cervical cancer of the uterus. In contradiction to the prior art, the assay of the present invention did not require extensive steps for DNA purification. Further, with the designed primers and the optimized conditions, the instant assay was shown to be specific for HSV-2 without cross-reactivity with other herpesviruses, human genomic sequences or HPV DNA The in vitro endpoint sensitivity of the assay reached 1 copy of HSV-2 DNA.

As in other PCR assays, some culture-negative samples were PCR-positive. The presence of sequences from another ORF of HSV-2 was documented in both culture-negative specimens, suggesting the presence of virus that could not be recovered by culture. To confirm the presence of HSV-2 DNA in culture-negative yet Xho-2-positive specimens, a second PCR test against another region of the HSV-2 genome was used in order to exclude positive reactions due to carryover of PCR products. This standard test amplifies a segment of the DNA polymerase gene of HSV-2 , a gene essential for viral replication and containing highly conserved sequences. False-positive results with PCR from contamination was not a problem during this study as evidenced by the repeatedly negative controls. Amplification of β-globin sequences also allowed to control for the integrity of cellular DNA and the quantity of cellular material treated in the sample (Galloway et al., 1984, Proc. Natl. Acad. Sci. USA 81:4736–4740).This PCR assay can also detect HSV-2 DNA sequences for longer periods than viral culture. Culture reaches equivalent sensitivity to direct detection assays if inoculation is performed immediately. A delay up to 18 hrs sometimes occurred in our study before inoculation for cell culture. This time frame represents more closely the usual clinical situation and could favour direct detection tests because of loss of viability due to culture delay.

There is an interest in detecting specifically transforming regions of HSV-2 in clinical samples, since other regions of the HSV-2 genome do not seem to be retained in tumoral tissue even when PCR is used to detect them. One group used PCR for the detection in clinical samples of a BC 24 DNA fragment located at the left-end of BglII N (Yamakawa et al., 1994, APMIS 102:401–406). HSV-2 DNA sequences were amplified from 14% of uterine cervix squamous cell carcinoma, 40% of cervical intraepithelial lesions, and 27% of cervical adenocarcinomas. Only 2 of the 15 samples containing HSV-2 BglII N sequences also contained HSV-2 DNA polymerase sequences (Yamakawa et al., 1994). All the HSV-2-positive samples also contained HPV16 or −18 sequences. Thus, HSV-2 could be considered as a cofactor in the cervical cancer for a subset of women.

One of the goal of the present invention was to identify the molecular determinant responsible for the tumorigenicity of the HPV-HSV-2 combination on cervical cells. The showing that the Xho-2 sequence transforms HIV-immortalized cervical cells demonstrates the importance of this HSV-2 molecular determinant in genital cancer development. Another goal of the present invention was to optimize and validate an assay that will allow the appropriate investigation of the role of HSV-2 as a co-factor in genital cancers. The herein disclosed PCR assay is the first assay which enables the detection of HSV-2 DNA sequences from the right-end of the fragment BglII N. the candidate responsible for the transforming ability of HSV-2 in vivo.

The present invention therefore provides research, diagnostic and therapeutic tools for detecting and typing HSV-2 as well as for detecting, understanding and preventing the transforming activity of HSV-2 Xho-2.

Although the present invention has been described hereinabove by way of preferred embodiments thereof, it can be modified, without departing from the spirit and nature of the subject invention as defined in the appended claims.

What is claimed is:

1. A method of detecting HSV-2 nucleic acid that specifically hybridizes to Xho-2 subfragment of BglII N fragment of HSV-2 nucleic acid in a sample comprising:
   (a) contacting said sample with an isolated nucleic acid molecule selected within the predicted open reading frame of Xho-2 subfragment of BglII N fragment of HSV-2 consisting of at least 15 nucleotides which specifically hybridizes to RNA or DNA encoding Xho-2 subfragment of BglII N fragment of HSV-2, wherein said nucleic acid molecule is, or is complementary to, a nucleotide sequence consisting of at least 15 consecutive nucleotides within the predicted open reading frame of Xho-2 subfragment of BglII N fragment of HSV-2, under conditions such that hybridization occurs, and
   (b) detecting the presence of said HSV-2 nucleic acid that specifically hybridizes to Xho-2 subfragment of BglII N fragment of HSV-2 nucleic acid.

2. A method of detecting HSV-2 nucleic acid that specifically hybridizes to Xho-2 subfragment of BglII N fragment of HSV-2 nucleic acid in a sample comprising:
   (a) contacting said sample with two different nucleic acid molecules, wherein each nucleic acid molecule is an isolated nucleic acid molecule selected within the predicted open reading frame of Xho-2 subfragment of BglII N fragment of HSV-2 consisting of at least 15 nucleotides which specifically hybridizes to RNA or DNA encoding Xho-2 subfragment of BglII N fragment of HSV-2, wherein said nucleic acid molecule is, or is complementary to, a nucleotide sequence consisting of at least 15 consecutive nucleotides within the predicted open reading frame of Xho-2 subfragment of BglII N fragment of HSV-2, under conditions such that a target sequence between said two different nucleic acid molecules is amplified from said sample; and
   (b) detecting the presence of said HSV-2 nucleic acid that specifically hybridizes to Xho-2 subfragment of BglII N fragment of HSV-2 nucleic acid.

3. The method according to claim 2, wherein said two different nucleic acid molecules comprise a nucleic acid sequence given herein as:
   Xho-a: 5'-AACACTGCCTCGGAGGGGATGAT-3'; SEQ. ID. No.:3; and Xho-b: 5'-AGGCCGGTGCTCCCGATCACGAA-3'; SEQ. ID No.:4; and said detecting in b) is carried out using a probe comprising a nucleic acid sequence given herein as:

Xho-p: 5'-TTCGTGGGGTCTGTCGTTCTGT-3'; SEQ. ID. No.:5.

4. The method according to claim 3, wherein the amplification is carried out by polymerase chain reaction.

5. The method according to claim 2, wherein said sample is submitted to a preparation step comprising centrifugation, resuspension, and treatment with detergent solution and proteinase K prior to step (a).

6. A purified polypeptide encoded by the open reading frame of Xho-2 subfragment of BglII N fragment of HSV-2 comprising an amino acid sequence at least 90% identical to the amino acid sequence of the polypeptide encoded by the open reading frame of Xho-2 subfragment of BglII N fragment of HSV-2 comprising the complete amino acid sequence defined in SEQ. ID. No.:2, wherein the polypeptide generates antibodies having specific binding affinity for the polypeptide encoded by the open reading frame of Xho-2 subfragment of BglII fragment of HSV-2 comprising the complete amino acid sequence defined in SEQ ID NO:2.

7. A purified polypeptide encoded by the open reading frame of Xho-2 subfragment of BglII N fragment of HSV-2 comprising the complete amino acid sequence defined in SEQ. ID. No.:2.

8. A method of typing a nucleic acid sample comprising:

(a) contacting said nucleic acid sample with an isolated nucleic acid molecule under conditions permitting a hybridization of said nucleic acid molecule to said nucleic acid sample, wherein said nucleic acid molecule is selected from the group consisting of:

(i) a nucleic acid molecule selected within the predicted open reading frame of Xho-2 subfragment of BglII N fragment of HSV-2 consisting of at least 15 nucleotides which specifically hybridizes to RNA or DNA encoding Xho-2 subfragment of BglII N fragment of HSV-2, wherein said nucleic acid molecule is, or is complementary to, a nucleotide sequence consisting of at least 15 consecutive nucleotides within the predicted open reading frame of Xho-2 subfragment of BglII N fragment of HSV-2;

(ii) Xho-a:
5'-AACACTGCCTCGGAGGGGATGAT-3';
SEQ. ID. No.:3;

(iii) Xho-b:
5'-AGGCCGGTGCTCCCGATCACGM-3';
SEQ. ID. No.: 4;

(iv) Xho-p:
5'-TTCGTGGGGTCTGTCGTTCTGT-3';
SEQ. ID. No.: 5; and any combination thereof; and (b) detecting the binding of said nucleic acid molecule to said nucleic acid sample, the binding thereof indicating that said nucleic acid sample contains HSV-2 nucleic acid.

* * * * *

UNITED STATES PATENT AND TRADEMARK OFFICE
CERTIFICATE OF CORRECTION

PATENT NO. : 6,617,103 B1
DATED : September 9, 2003
INVENTOR(S) : Kessous et al.

It is certified that error appears in the above-identified patent and that said Letters Patent is hereby corrected as shown below:

Column 34,
Line 42, delete "M" and replace with -- AA --.

Signed and Sealed this

Twenty-second Day of March, 2005

JON W. DUDAS
*Director of the United States Patent and Trademark Office*